(12) United States Patent
Yadin

(10) Patent No.: US 7,842,082 B2
(45) Date of Patent: Nov. 30, 2010

(54) BIFURCATED STENT

(75) Inventor: Amnon Yadin, Kfar Vitkin (IL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 48 days.

(21) Appl. No.: 11/848,171

(22) Filed: Aug. 30, 2007

(65) Prior Publication Data
US 2008/0119925 A1    May 22, 2008

Related U.S. Application Data

(60) Provisional application No. 60/859,460, filed on Nov. 16, 2006.

(51) Int. Cl.
*A61F 2/06* (2006.01)
(52) U.S. Cl. ..................... 623/1.35; 623/1.15
(58) Field of Classification Search ................ 623/1.35, 623/1.15
See application file for complete search history.

(56) References Cited

U.S. PATENT DOCUMENTS

| | | | |
|---|---|---|---|
| 4,309,994 A | 1/1982 | Grunwald |
| 4,769,005 A | 9/1988 | Ginsburg et al. |
| 4,774,949 A | 10/1988 | Fogarty |
| 4,896,670 A | 1/1990 | Crittenden |
| 4,905,667 A | 3/1990 | Foerster et al. |
| 4,906,244 A | 3/1990 | Pinchuk et al. |
| 4,935,190 A | 6/1990 | Tennerstedt |
| 4,994,071 A | 2/1991 | MacGregor |
| 5,037,392 A | 8/1991 | Hillstead |
| 5,053,007 A | 10/1991 | Euteneuer |
| 5,087,246 A | 2/1992 | Smith |
| 5,112,900 A | 5/1992 | Buddenhagen et al. |
| 5,147,302 A | 9/1992 | Euteneuer et al. |
| 5,163,989 A | 11/1992 | Campbell et al. |

(Continued)

FOREIGN PATENT DOCUMENTS

CA    2220864    7/1999

(Continued)

OTHER PUBLICATIONS

U.S. Appl. No. 60/844,011, filed Sep. 12, 2006; Inventor: Broome et al.

(Continued)

*Primary Examiner*—David Isabella
*Assistant Examiner*—Jacqueline Woznicki
(74) *Attorney, Agent, or Firm*—Vidas, Arrett & Steinkraus

(57) ABSTRACT

In at least one other embodiment, a stent comprises a plurality of interconnected framework members defining a plurality of cells. A portion of the interconnected framework members comprise a side branch structure defining an inner side branch cell that is shaped differently from other cells of the stent. The side branch structure comprises a first serpentine ring, a second serpentine ring and a plurality of side branch connectors. The first serpentine ring extends around the inner side branch cell and comprises alternating inner turns and outer turns. The second serpentine ring extends around the first serpentine ring and comprises alternating inner turns and outer turns. The second serpentine ring has the same number of outer turns as the first serpentine ring. Each side branch connector spans between the first serpentine ring and the second serpentine ring in a side branch radial direction.

20 Claims, 25 Drawing Sheets

U.S. PATENT DOCUMENTS

| | | |
|---|---|---|
| 5,209,799 A | 5/1993 | Vigil |
| 5,226,887 A | 7/1993 | Farr et al. |
| 5,306,246 A | 4/1994 | Sahatijian et al. |
| 5,318,587 A | 6/1994 | Davey |
| 5,342,307 A | 8/1994 | Euteneuer et al. |
| 5,342,387 A | 8/1994 | Summers |
| 5,348,538 A | 9/1994 | Wang et al. |
| 5,350,361 A | 9/1994 | Tsukashima et al. |
| 5,358,475 A | 10/1994 | Mares et al. |
| 5,387,235 A | 2/1995 | Chuter |
| 5,403,340 A | 4/1995 | Wang et al. |
| 5,447,497 A | 9/1995 | Sogard et al. |
| 5,456,666 A | 10/1995 | Campbell et al. |
| 5,456,712 A | 10/1995 | Maginot |
| 5,458,572 A | 10/1995 | Campbell et al. |
| 5,476,471 A | 12/1995 | Shifrin et al. |
| 5,478,319 A | 12/1995 | Campbell et al. |
| 5,487,730 A | 1/1996 | Marcadis et al. |
| 5,523,092 A | 6/1996 | Hanson et al. |
| 5,549,552 A | 8/1996 | Peters et al. |
| 5,550,180 A | 8/1996 | Elsik et al. |
| 5,556,383 A | 9/1996 | Wang et al. |
| 5,591,228 A | 1/1997 | Edoga |
| 5,607,444 A | 3/1997 | Lam |
| 5,609,605 A | 3/1997 | Marshall et al. |
| 5,609,627 A | 3/1997 | Goicoechea et al. |
| 5,613,980 A | 3/1997 | Chauhan |
| 5,617,878 A | 4/1997 | Taheri |
| 5,632,762 A | 5/1997 | Myler |
| 5,632,763 A | 5/1997 | Glastra |
| 5,632,772 A | 5/1997 | Alcime et al. |
| 5,636,641 A | 6/1997 | Fariabi |
| 5,669,924 A | 9/1997 | Shaknovich |
| 5,669,932 A | 9/1997 | Fischell et al. |
| 5,676,697 A | 10/1997 | McDonald |
| 5,683,450 A | 11/1997 | Goicoechea et al. |
| 5,697,971 A | 12/1997 | Fischell et al. |
| 5,707,348 A | 1/1998 | Krogh |
| 5,709,713 A | 1/1998 | Evans et al. |
| 5,718,684 A | 2/1998 | Gupta |
| 5,718,724 A | 2/1998 | Goicoechea et al. |
| 5,720,735 A | 2/1998 | Dorros |
| 5,746,745 A | 5/1998 | Abele et al. |
| 5,749,825 A | 5/1998 | Fischell et al. |
| 5,749,890 A | 5/1998 | Shaknovich |
| 5,755,734 A | 5/1998 | Richter et al. |
| 5,755,735 A | 5/1998 | Richter et al. |
| 5,755,771 A | 5/1998 | Penn et al. |
| 5,755,773 A | 5/1998 | Evans et al. |
| 5,755,778 A | 5/1998 | Kleshinski |
| 5,782,906 A | 7/1998 | Marshall et al. |
| 5,800,520 A | 9/1998 | Fogarty et al. |
| 5,810,767 A | 9/1998 | Klein |
| 5,824,036 A | 10/1998 | Lauterjung |
| 5,824,040 A | 10/1998 | Cox et al. |
| 5,827,320 A | 10/1998 | Richter et al. |
| 5,830,182 A | 11/1998 | Wang et al. |
| 5,833,657 A | 11/1998 | Reinhardt et al. |
| 5,843,172 A | 12/1998 | Yan |
| 5,851,464 A | 12/1998 | Davila et al. |
| 5,868,777 A | 2/1999 | Lam |
| 5,882,334 A | 3/1999 | Sepetka et al. |
| 5,891,108 A | 4/1999 | Leone et al. |
| 5,893,887 A | 4/1999 | Jayaraman |
| 5,906,640 A | 5/1999 | Penn et al. |
| 5,922,020 A | 7/1999 | Klein et al. |
| 5,922,021 A | 7/1999 | Jang |
| 5,951,941 A | 9/1999 | Wang et al. |
| 5,961,548 A | 10/1999 | Shmulewitz |
| 5,972,017 A | 10/1999 | Berg et al. |
| 5,972,027 A | 10/1999 | Johnson |
| 6,013,054 A | 1/2000 | Jiun Yan |
| 6,013,055 A | 1/2000 | Bampos et al. |
| 6,013,091 A | 1/2000 | Ley et al. |
| 6,017,324 A | 1/2000 | Tu et al. |
| 6,017,363 A | 1/2000 | Hojeibane |
| 6,030,414 A | 2/2000 | Taheri |
| 6,033,380 A | 3/2000 | Butaric et al. |
| 6,033,433 A | 3/2000 | Ehr et al. |
| 6,033,434 A | 3/2000 | Borghi |
| 6,033,435 A | 3/2000 | Penn et al. |
| 6,048,361 A | 4/2000 | Von Oepen |
| 6,056,775 A | 5/2000 | Borghi et al. |
| 6,059,824 A | 5/2000 | Taheri |
| 6,068,655 A | 5/2000 | Seguin et al. |
| 6,071,285 A | 6/2000 | Lashinski et al. |
| 6,071,305 A | 6/2000 | Brown et al. |
| 6,086,611 A | 7/2000 | Duffy et al. |
| 6,093,203 A | 7/2000 | Uflacker |
| 6,096,070 A | 8/2000 | Ragheb et al. |
| 6,096,073 A | 8/2000 | Webster et al. |
| 6,099,497 A | 8/2000 | Adams et al. |
| 6,113,579 A | 9/2000 | Eidenschink et al. |
| 6,117,117 A | 9/2000 | Mauch |
| 6,117,156 A | 9/2000 | Richter et al. |
| 6,123,721 A | 9/2000 | Jang |
| 6,126,652 A | 10/2000 | McLeod et al. |
| 6,129,738 A | 10/2000 | Lashinski et al. |
| 6,129,754 A | 10/2000 | Kanesaka et al. |
| 6,135,982 A | 10/2000 | Campbell |
| 6,142,973 A | 11/2000 | Carleton et al. |
| 6,143,002 A | 11/2000 | Vietmeier |
| 6,146,356 A | 11/2000 | Wang et al. |
| 6,159,238 A | 12/2000 | Killion et al. |
| 6,165,195 A | 12/2000 | Wilson et al. |
| 6,168,621 B1 | 1/2001 | Vrba |
| 6,171,278 B1 | 1/2001 | Wang et al. |
| 6,183,509 B1 | 2/2001 | Dibie |
| 6,190,404 B1 | 2/2001 | Palmaz et al. |
| 6,203,568 B1 | 3/2001 | Lombardi et al. |
| 6,206,915 B1 | 3/2001 | Fagan et al. |
| 6,206,916 B1 | 3/2001 | Furst |
| 6,210,380 B1 | 4/2001 | Mauch |
| 6,210,429 B1 | 4/2001 | Vardi et al. |
| 6,210,433 B1 | 4/2001 | Larre |
| 6,210,436 B1 | 4/2001 | Weadock |
| 6,231,598 B1 | 5/2001 | Berry et al. |
| 6,240,616 B1 | 6/2001 | Yan |
| 6,241,762 B1 | 6/2001 | Shanley |
| 6,253,443 B1 | 7/2001 | Johnson |
| 6,254,593 B1 | 7/2001 | Wilson |
| 6,254,632 B1 | 7/2001 | Wu et al. |
| 6,258,115 B1 | 7/2001 | Dubrul |
| 6,258,116 B1 | 7/2001 | Hojeibane |
| 6,258,121 B1 | 7/2001 | Yang et al. |
| 6,261,305 B1 | 7/2001 | Marotta et al. |
| 6,261,316 B1 | 7/2001 | Shaolian et al. |
| 6,261,320 B1 | 7/2001 | Tam et al. |
| 6,264,662 B1 | 7/2001 | Lauterjung |
| 6,264,686 B1 | 7/2001 | Rieu et al. |
| 6,273,908 B1 | 8/2001 | Ndondo-Lay |
| 6,273,913 B1 | 8/2001 | Wright et al. |
| 6,280,413 B1 | 8/2001 | Clark et al. |
| 6,287,628 B1 | 9/2001 | Hossainy et al. |
| 6,290,673 B1 | 9/2001 | Shanley |
| 6,293,967 B1 | 9/2001 | Shanley |
| 6,293,968 B1 | 9/2001 | Taheri |
| 6,325,822 B1 | 12/2001 | Chouinard et al. |
| 6,325,826 B1 | 12/2001 | Vardi et al. |
| 6,328,925 B1 | 12/2001 | Wang et al. |
| 6,334,864 B1 | 1/2002 | Amplatz et al. |
| 6,334,870 B1 | 1/2002 | Ehr et al. |
| 6,346,089 B1 | 2/2002 | Dibie |
| 6,348,065 B1 | 2/2002 | Brown et al. |

| | | |
|---|---|---|
| 6,355,060 B1 | 3/2002 | Lenker et al. |
| 6,358,552 B1 | 3/2002 | Mandralis et al. |
| 6,361,544 B1 | 3/2002 | Wilson et al. |
| 6,361,555 B1 | 3/2002 | Wilson |
| 6,379,381 B1 | 4/2002 | Hossainy et al. |
| 6,383,213 B2 | 5/2002 | Wilson et al. |
| 6,395,018 B1 | 5/2002 | Castaneda |
| 6,395,326 B1 | 5/2002 | Castro et al. |
| 6,406,457 B1 | 6/2002 | Wang et al. |
| 6,423,091 B1 | 7/2002 | Hojeibane |
| 6,436,104 B2 | 8/2002 | Hojeibane |
| 6,436,134 B2 | 8/2002 | Richter et al. |
| 6,478,816 B1 | 11/2002 | Kveen et al. |
| 6,491,666 B1 | 12/2002 | Santini, Jr. et al. |
| 6,506,437 B1 | 1/2003 | Harish et al. |
| 6,508,836 B2 | 1/2003 | Wilson et al. |
| 6,517,558 B2 | 2/2003 | Gittings et al. |
| 6,520,988 B1 | 2/2003 | Colombo et al. |
| 6,527,762 B1 | 3/2003 | Santini, Jr. et al. |
| 6,527,799 B2 | 3/2003 | Shanley |
| 6,537,256 B2 | 3/2003 | Santini, Jr. et al. |
| 6,540,779 B2 | 4/2003 | Richter et al. |
| 6,551,351 B2 | 4/2003 | Smith et al. |
| 6,551,838 B2 | 4/2003 | Santini, Jr. et al. |
| 6,558,422 B1 | 5/2003 | Baker et al. |
| 6,562,065 B1 | 5/2003 | Shanley |
| 6,579,309 B1 | 6/2003 | Loos et al. |
| 6,579,312 B2 | 6/2003 | Wilson et al. |
| 6,582,394 B1 | 6/2003 | Reiss et al. |
| 6,596,020 B2 | 7/2003 | Vardi et al. |
| 6,599,316 B2 | 7/2003 | Vardi et al. |
| 6,638,302 B1 | 10/2003 | Curcio et al. |
| 6,645,242 B1 | 11/2003 | Quinn |
| 6,656,162 B2 | 12/2003 | Santini, Jr. et al. |
| 6,669,683 B2 | 12/2003 | Santini, Jr. et al. |
| 6,689,156 B1 | 2/2004 | Davidson et al. |
| 6,692,483 B2 | 2/2004 | Vardi et al. |
| 6,695,877 B2 | 2/2004 | Brucker et al. |
| 6,706,062 B2 | 3/2004 | Vardi et al. |
| 6,709,379 B1 | 3/2004 | Brandau et al. |
| 6,713,119 B2 | 3/2004 | Hossainy et al. |
| 6,730,064 B2 | 5/2004 | Ragheb et al. |
| 6,749,628 B1 | 6/2004 | Cho et al. |
| 6,758,859 B1 | 7/2004 | Dang et al. |
| 6,764,507 B2 | 7/2004 | Shanley et al. |
| 6,773,429 B2 | 8/2004 | Sheppard, Jr. et al. |
| 6,776,793 B2 | 8/2004 | Brown et al. |
| 6,783,543 B2 | 8/2004 | Jang |
| 6,790,228 B2 | 9/2004 | Hossainy et al. |
| 6,811,566 B1 | 11/2004 | Penn et al. |
| 6,827,250 B2 | 12/2004 | Uhland et al. |
| 6,835,203 B1 | 12/2004 | Vardi et al. |
| 6,858,038 B2 | 2/2005 | Heuser |
| 6,884,258 B2 | 4/2005 | Vardi et al. |
| 6,896,699 B2 | 5/2005 | Wilson et al. |
| 6,904,658 B2 | 6/2005 | Hines |
| 6,932,837 B2 | 8/2005 | Amplatz et al. |
| 6,946,092 B1 | 9/2005 | Bertolino et al. |
| 6,955,687 B2 | 10/2005 | Richter et al. |
| 6,955,688 B2 | 10/2005 | Wilson et al. |
| 6,962,602 B2 | 11/2005 | Vardi et al. |
| 6,989,071 B2 | 1/2006 | Kocur et al. |
| 7,018,400 B2 | 3/2006 | Lashinski et al. |
| 7,041,130 B2 | 5/2006 | Santini, Jr. et al. |
| 7,052,488 B2 | 5/2006 | Uhland |
| 7,056,323 B2 | 6/2006 | Mareiro et al. |
| 7,056,388 B2 | 6/2006 | Franken et al. |
| 7,060,091 B2 | 6/2006 | Killion et al. |
| 7,070,616 B2 | 7/2006 | Majercak et al. |
| 7,118,593 B2 * | 10/2006 | Davidson et al. ........... 623/1.15 |
| 7,160,321 B2 | 1/2007 | Shanley |
| 7,169,175 B2 | 1/2007 | Cottone, Jr. et al. |
| 7,169,179 B2 | 1/2007 | Shanley et al. |
| 7,179,288 B2 | 2/2007 | Shanley |
| 7,179,289 B2 | 2/2007 | Shanley |
| 7,208,010 B2 | 4/2007 | Shanley et al. |
| 7,208,011 B2 | 4/2007 | Shanley et al. |
| 7,220,275 B2 | 5/2007 | Davidson et al. |
| 7,341,598 B2 * | 3/2008 | Davidson et al. ........... 623/1.35 |
| 2001/0003161 A1 | 6/2001 | Vardi et al. |
| 2001/0004706 A1 | 6/2001 | Hojeibane |
| 2001/0004707 A1 | 6/2001 | Dereume et al. |
| 2001/0012927 A1 | 8/2001 | Mauch |
| 2001/0016766 A1 | 8/2001 | Vardi et al. |
| 2001/0016767 A1 | 8/2001 | Wilson et al. |
| 2001/0016768 A1 | 8/2001 | Wilson et al. |
| 2001/0025195 A1 | 9/2001 | Shaolian et al. |
| 2001/0027291 A1 | 10/2001 | Shanley |
| 2001/0027338 A1 | 10/2001 | Greenberg |
| 2001/0029396 A1 | 10/2001 | Wilson et al. |
| 2001/0037116 A1 | 11/2001 | Wilson et al. |
| 2001/0037138 A1 | 11/2001 | Wilson et al. |
| 2001/0039448 A1 | 11/2001 | Dibie |
| 2001/0049552 A1 | 12/2001 | Richter et al. |
| 2001/0056297 A1 | 12/2001 | Hojeibane |
| 2002/0013618 A1 | 1/2002 | Marotta et al. |
| 2002/0013619 A1 | 1/2002 | Shanley |
| 2002/0022874 A1 | 2/2002 | Wilson |
| 2002/0026232 A1 | 2/2002 | Marotta et al. |
| 2002/0035392 A1 | 3/2002 | Wilson |
| 2002/0038146 A1 | 3/2002 | Harry |
| 2002/0042650 A1 | 4/2002 | Vardi et al. |
| 2002/0052648 A1 | 5/2002 | McGuckin, Jr. et al. |
| 2002/0072790 A1 | 6/2002 | McGuckin, Jr. et al. |
| 2002/0095208 A1 | 7/2002 | Gregorich et al. |
| 2002/0111675 A1 | 8/2002 | Wilson |
| 2002/0156516 A1 | 10/2002 | Vardi et al. |
| 2002/0156517 A1 | 10/2002 | Perouse |
| 2002/0163104 A1 | 11/2002 | Motsenbocker et al. |
| 2002/0165604 A1 | 11/2002 | Shanley |
| 2002/0173835 A1 | 11/2002 | Bourang et al. |
| 2002/0173840 A1 | 11/2002 | Brucker et al. |
| 2002/0183763 A1 | 12/2002 | Callol et al. |
| 2002/0193872 A1 | 12/2002 | Trout, III et al. |
| 2002/0193873 A1 | 12/2002 | Brucker et al. |
| 2003/0009209 A1 | 1/2003 | Hojeibane |
| 2003/0028233 A1 | 2/2003 | Vardi et al. |
| 2003/0050688 A1 | 3/2003 | Fischell et al. |
| 2003/0055378 A1 | 3/2003 | Wang et al. |
| 2003/0055483 A1 | 3/2003 | Gumm |
| 2003/0074047 A1 | 4/2003 | Richter |
| 2003/0083687 A1 | 5/2003 | Pallazza |
| 2003/0093109 A1 | 5/2003 | Mauch |
| 2003/0097169 A1 | 5/2003 | Brucker et al. |
| 2003/0105511 A1 | 6/2003 | Welsh et al. |
| 2003/0114912 A1 | 6/2003 | Sequin et al. |
| 2003/0125791 A1 | 7/2003 | Sequin et al. |
| 2003/0125802 A1 | 7/2003 | Callol et al. |
| 2003/0135259 A1 | 7/2003 | Simso |
| 2003/0163157 A1 | 8/2003 | McMorrow et al. |
| 2003/0167085 A1 | 9/2003 | Shanley |
| 2003/0181923 A1 | 9/2003 | Vardi |
| 2003/0195606 A1 | 10/2003 | Davidson et al. |
| 2003/0199970 A1 | 10/2003 | Shanley |
| 2004/0006381 A1 | 1/2004 | Sequin et al. |
| 2004/0015227 A1 | 1/2004 | Vardi et al. |
| 2004/0044396 A1 | 3/2004 | Clerc et al. |
| 2004/0059406 A1 | 3/2004 | Cully et al. |
| 2004/0068161 A1 | 4/2004 | Couvillon, Jr. |
| 2004/0073294 A1 | 4/2004 | Diaz et al. |
| 2004/0088007 A1 | 5/2004 | Eidenschink |
| 2004/0093071 A1 | 5/2004 | Jang |
| 2004/0117003 A1 | 6/2004 | Ouriel et al. |
| 2004/0122505 A1 | 6/2004 | Shanley |
| 2004/0122506 A1 | 6/2004 | Shanley et al. |
| 2004/0127976 A1 | 7/2004 | Diaz |

| Publication No. | Date | Name |
|---|---|---|
| 2004/0127977 A1 | 7/2004 | Shanley |
| 2004/0133268 A1 | 7/2004 | Davidson et al. |
| 2004/0138732 A1 | 7/2004 | Suhr et al. |
| 2004/0138737 A1 | 7/2004 | Davidson et al. |
| 2004/0142014 A1 | 7/2004 | Livack et al. |
| 2004/0143321 A1 | 7/2004 | Livack et al. |
| 2004/0143322 A1 | 7/2004 | Livack et al. |
| 2004/0148006 A1 | 7/2004 | Davidson et al. |
| 2004/0148012 A9 | 7/2004 | Jang |
| 2004/0172121 A1 | 9/2004 | Eidenschink et al. |
| 2004/0186560 A1 | 9/2004 | Alt |
| 2004/0202692 A1 | 10/2004 | Shanley et al. |
| 2004/0204750 A1 | 10/2004 | Dinh |
| 2004/0215227 A1 | 10/2004 | McMorrow et al. |
| 2004/0220661 A1 | 11/2004 | Shanley et al. |
| 2004/0225345 A1 | 11/2004 | Fischell et al. |
| 2004/0236408 A1 | 11/2004 | Shanley |
| 2004/0249449 A1 | 12/2004 | Shanley et al. |
| 2004/0267352 A1 | 12/2004 | Davidson et al. |
| 2005/0004656 A1 | 1/2005 | Das |
| 2005/0010278 A1 | 1/2005 | Vardi et al. |
| 2005/0015108 A1 | 1/2005 | Williams et al. |
| 2005/0015135 A1 | 1/2005 | Shanley |
| 2005/0043816 A1 | 2/2005 | Datta et al. |
| 2005/0060027 A1* | 3/2005 | Khenansho et al. ........ 623/1.35 |
| 2005/0096726 A1 | 5/2005 | Sequin et al. |
| 2005/0102017 A1 | 5/2005 | Mattison |
| 2005/0102021 A1 | 5/2005 | Osborne |
| 2005/0102023 A1 | 5/2005 | Yadin et al. |
| 2005/0119731 A1 | 6/2005 | Brucker et al. |
| 2005/0125076 A1 | 6/2005 | Ginn |
| 2005/0131526 A1 | 6/2005 | Wong |
| 2005/0149161 A1 | 7/2005 | Eidenschink et al. |
| 2005/0154442 A1 | 7/2005 | Eidenschink et al. |
| 2005/0154444 A1 | 7/2005 | Quadri |
| 2005/0183259 A1 | 8/2005 | Eidenschink et al. |
| 2005/0187602 A1 | 8/2005 | Eidenschink |
| 2005/0187611 A1 | 8/2005 | Ding et al. |
| 2005/0192657 A1 | 9/2005 | Colen et al. |
| 2005/0209673 A1 | 9/2005 | Shaked |
| 2005/0222668 A1 | 10/2005 | Schaeffer et al. |
| 2005/0228483 A1 | 10/2005 | Kaplan et al. |
| 2005/0273149 A1 | 12/2005 | Tran et al. |
| 2006/0015134 A1 | 1/2006 | Trinidad |
| 2006/0034884 A1 | 2/2006 | Stenzel |
| 2006/0036315 A1* | 2/2006 | Yadin et al. ................ 623/1.35 |
| 2006/0041303 A1 | 2/2006 | Israel |
| 2006/0045901 A1 | 3/2006 | Weber |
| 2006/0079956 A1 | 4/2006 | Eigler et al. |
| 2006/0088654 A1 | 4/2006 | Ding et al. |
| 2006/0093643 A1 | 5/2006 | Stenzel |
| 2006/0100686 A1 | 5/2006 | Bolduc |
| 2006/0122698 A1 | 6/2006 | Spencer et al. |
| 2006/0173528 A1 | 8/2006 | Feld et al. |
| 2006/0206188 A1 | 9/2006 | Weber et al. |
| 2006/0287712 A1 | 12/2006 | Eidenschink |
| 2007/0005126 A1 | 1/2007 | Tischler |
| 2007/0050016 A1 | 3/2007 | Gregorich et al. |
| 2007/0073376 A1 | 3/2007 | Krolik et al. |
| 2007/0073384 A1 | 3/2007 | Brown et al. |
| 2007/0100434 A1 | 5/2007 | Gregorich et al. |
| 2007/0112418 A1 | 5/2007 | Eidenschink et al. |
| 2007/0112419 A1* | 5/2007 | Yadin .................... 623/1.35 |
| 2007/0142902 A1* | 6/2007 | Yadin .................... 623/1.16 |
| 2007/0173787 A1 | 7/2007 | Huang et al. |
| 2007/0173923 A1 | 7/2007 | Savage et al. |
| 2007/0208411 A1 | 9/2007 | Meyer et al. |
| 2007/0208414 A1 | 9/2007 | Sorenson et al. |
| 2007/0260303 A1* | 11/2007 | Hegg .................... 623/1.16 |
| 2008/0065197 A1* | 3/2008 | Meyer et al. ............... 623/1.16 |

FOREIGN PATENT DOCUMENTS

| | | |
|---|---|---|
| DE | 9014845 | 2/1991 |
| DE | 29701758 | 3/1997 |
| DE | 29701883 | 5/1997 |
| DE | 19921788 | 11/2000 |
| EP | 0479730 | 10/1991 |
| EP | 0565796 | 10/1993 |
| EP | 0751752 | 1/1997 |
| EP | 0783873 | 7/1997 |
| EP | 0804907 | 11/1997 |
| EP | 0479557 | 7/1998 |
| EP | 0876805 | 11/1998 |
| EP | 0880949 | 12/1998 |
| EP | 0891751 | 1/1999 |
| EP | 0895759 | 2/1999 |
| EP | 0904745 | 3/1999 |
| EP | 0937442 | 8/1999 |
| EP | 0950386 | 10/1999 |
| EP | 0347023 | 12/1999 |
| EP | 1031328 | 8/2000 |
| EP | 1031329 | 8/2000 |
| EP | 0883384 | 12/2000 |
| EP | 0862392 | 8/2001 |
| EP | 0808140 | 12/2001 |
| EP | 0884028 | 2/2002 |
| EP | 1190685 | 3/2002 |
| EP | 0897700 | 7/2002 |
| EP | 0684022 | 2/2004 |
| EP | 1157674 | 7/2005 |
| EP | 1031330 | 11/2005 |
| EP | 1070513 | 6/2006 |
| FR | 2678508 | 1/1993 |
| FR | 2740346 | 10/1995 |
| FR | 2756173 | 11/1996 |
| GB | 2337002 | 5/1998 |
| WO | 88/60626 | 8/1988 |
| WO | 94/23787 | 10/1994 |
| WO | 95/21592 | 8/1995 |
| WO | 96/29955 | 10/1996 |
| WO | 96/34580 | 11/1996 |
| WO | 96/41592 | 12/1996 |
| WO | 97/07752 | 3/1997 |
| WO | 97/15346 | 5/1997 |
| WO | 97/16217 | 5/1997 |
| WO | 97/26936 | 7/1997 |
| WO | 97/41803 | 11/1997 |
| WO | 97/45073 | 12/1997 |
| WO | 97/46174 | 12/1997 |
| WO | 98/19628 | 5/1998 |
| WO | 98/23228 | 6/1998 |
| WO | 98/36709 | 8/1998 |
| WO | 98/36784 | 8/1998 |
| WO | 98/37833 | 9/1998 |
| WO | 98/47447 | 10/1998 |
| WO | 98/48879 | 11/1998 |
| WO | 99/03426 | 1/1999 |
| WO | 99/04726 | 2/1999 |
| WO | 99/15103 | 4/1999 |
| WO | 99/15108 | 4/1999 |
| WO | 99/15109 | 4/1999 |
| WO | 99/23977 | 5/1999 |
| WO | 99/24104 | 5/1999 |
| WO | 99/29262 | 6/1999 |
| WO | 99/34749 | 7/1999 |
| WO | 99/36002 | 7/1999 |
| WO | 99/36015 | 7/1999 |
| WO | 99/44539 | 9/1999 |
| WO | 99/56661 | 11/1999 |
| WO | 99/65419 | 12/1999 |
| WO | 00/07523 | 2/2000 |

| | | |
|---|---|---|
| WO | 00/10489 | 3/2000 |
| WO | 00/16719 | 3/2000 |
| WO | 00/27307 | 5/2000 |
| WO | 00/27463 | 5/2000 |
| WO | 00/28922 | 5/2000 |
| WO | 01/45594 | 6/2000 |
| WO | 00/44307 | 8/2000 |
| WO | 00/44309 | 8/2000 |
| WO | 00/47134 | 8/2000 |
| WO | 00/48531 | 8/2000 |
| WO | 00/49951 | 8/2000 |
| WO | 00/51523 | 9/2000 |
| WO | 00/57813 | 10/2000 |
| WO | 00/67673 | 11/2000 |
| WO | 00/71054 | 11/2000 |
| WO | 00/71055 | 11/2000 |
| WO | 00/74595 | 12/2000 |
| WO | 01/17577 | 3/2001 |
| WO | 01/21095 | 3/2001 |
| WO | 01/21109 | 3/2001 |
| WO | 01/21244 | 3/2001 |
| WO | 01/26584 | 4/2001 |
| WO | 01/35715 | 5/2001 |
| WO | 01/35863 | 5/2001 |
| WO | 01/39697 | 6/2001 |
| WO | 01/39699 | 6/2001 |
| WO | 01/41677 | 6/2001 |
| WO | 01/43665 | 6/2001 |
| WO | 01/43809 | 6/2001 |
| WO | 01/45785 | 6/2001 |
| WO | 01/49342 | 7/2001 |
| WO | 01/54621 | 8/2001 |
| WO | 01/54622 | 8/2001 |
| WO | 01/58385 | 8/2001 |
| WO | 01/60284 | 8/2001 |
| WO | 01/66036 | 9/2001 |
| WO | 01/70294 | 9/2001 |
| WO | 01/70299 | 9/2001 |
| WO | 01/74273 | 10/2001 |
| WO | 01/89409 | 11/2001 |
| WO | 01/91918 | 12/2001 |
| WO | 01/93781 | 12/2001 |
| WO | 02/00138 | 1/2002 |
| WO | 02/053066 | 7/2002 |
| WO | 02/068012 | 9/2002 |
| WO | 03/007842 | 1/2003 |
| WO | 03/055414 | 7/2003 |
| WO | 03/063924 | 8/2003 |
| WO | 2004/026174 | 4/2004 |
| WO | 2004/026180 | 4/2004 |
| WO | 2005/009295 | 2/2005 |
| WO | 2005/014077 | 2/2005 |
| WO | 2005/041810 | 5/2005 |
| WO | 2005/122959 | 12/2005 |
| WO | 2006/028925 | 3/2006 |
| WO | 2006/077476 | 7/2006 |
| WO | 2006/127127 | 11/2006 |

OTHER PUBLICATIONS

U.S. Appl. No. 09/663,111, filed Sep. 15, 2000; Inventor: Davidson et al.
U.S. Appl. No. 09/614,472, filed Jul. 11, 2000; Inventor: Davidson et al.
U.S. Appl. No. 09/325,996, filed Jun. 4, 1999; Inventor: Vardi et al.
Chevalier, M.D., Bernard, "Placement of Coronary Stents in Bifurcation Lesions by the "Culotte" Technique," The American Journal of Cardiology, vol. 82, pp. 943-949 (Oct. 15, 1998).
Nakamura M.D., Shigeru, "Techniques for Palmaz-Schatz Stent Deployment in Lesions with a Large Side Branch," Catheterization and Cardiovascular Diagnosis, vol. 34, pp. 353-361 (1995).
Caputo, Ronald P., "Stent Jail: A Minimum-Security Prison," The American Journal of Cardiology, vol. 77, pp. 1226-1230 (Jun. 1, 1996).
Colombo, M.D., Antonio, ""Kissing" Stent for Bifurcational Coronary Lesions," Catheterization and Cardiovascular Diagnosis, vol. 30, pp. 327-330 (Dec. 1993).
Carrie, M.D., Didier, ""T"-Shaped Stent Placement: A Technique for the Treatment of Dissected Bifurcation Lesions," Catheterization and Cardiovascular Diagnosis, vol. 37 pp. 311-313 (Mar. 1996).
Katoh, M.D., Osamu, "New Double Wire Technique to Stent Ostial Lesions," Catheterization and Cardiovascular Diagnosis, vol. 40, pp. 400-402 (Apr. 1997).
Lewis, M.D., Bruce E., "Acute procedural results in the treatment of 30 coronary atery bifurcation lesions with a double-wire atherectomy technique for side-branch protection," American Heart Journal, vol. 127:6, pp. 1600-1607 (Jun. 1994).
Yamashita, M.D., PhD., Takehiro, "Bifurcation Lesions: Two Stents Versus One Stent—Immediate and Follow-up Results," Journal of the American College of Cardiology, vol. 35:5, pp. 1145-1151 (Apr. 2000).
Satler, M.D., Lowell F., "Bifurcation Disease: To Treat or Not to Treat," Catheterization and Cardiovascular Interventions, vol. 50, pp. 411-412 (2000).

* cited by examiner

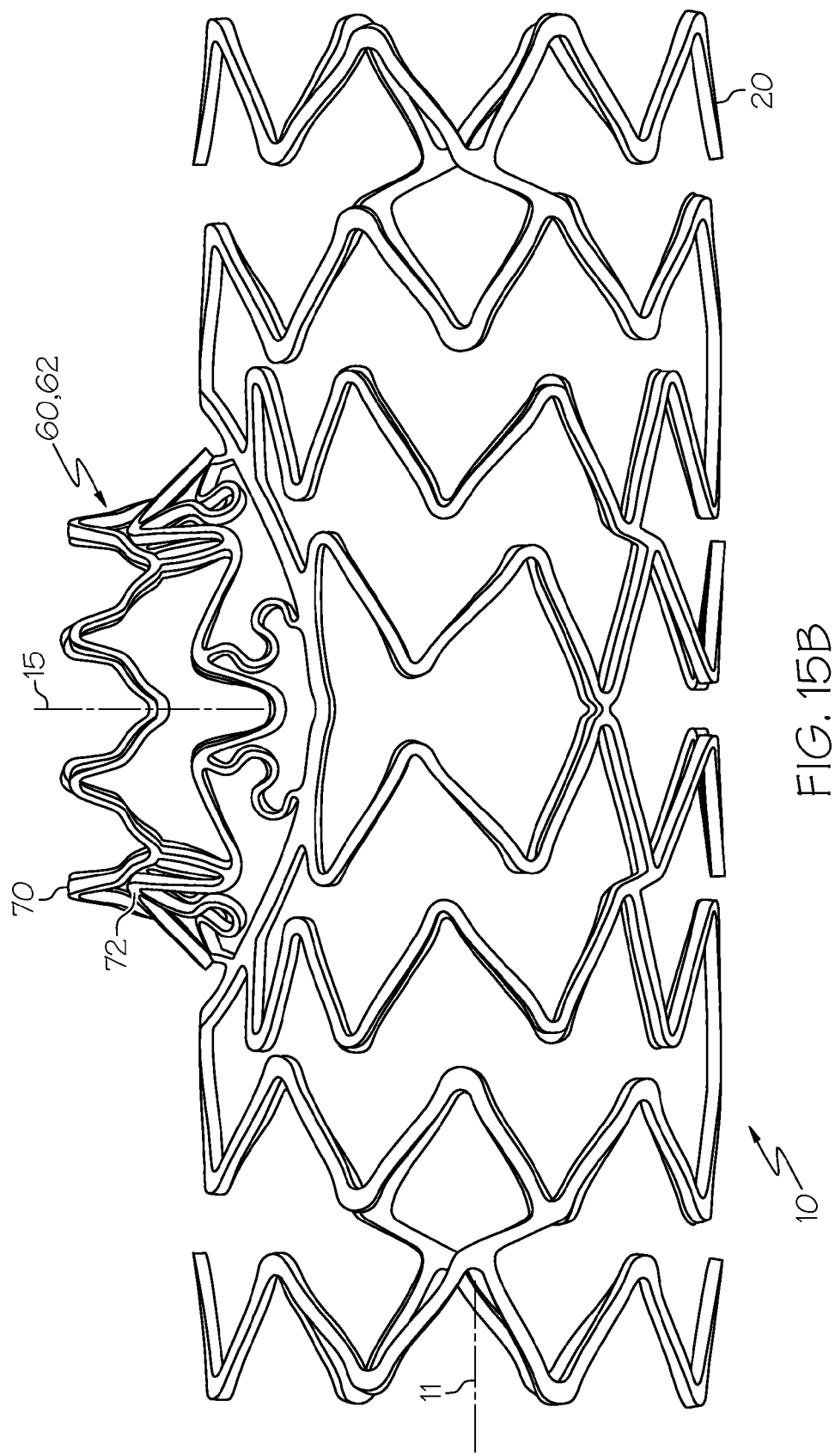

BIFURCATED STENT

CROSS-REFERENCE TO RELATED APPLICATIONS

This Application claims the benefit of and priority to U.S. Provisional Application No. 60/859,460, filed Nov. 16, 2006, the entire disclosure of which is hereby incorporated herein by reference in its entirety.

STATEMENT REGARDING FEDERALLY SPONSORED RESEARCH

Not Applicable

BACKGROUND OF THE INVENTION

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

There remains a need for novel stent designs that are suitable for use at a vessel bifurcation.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, a stent comprises a plurality of interconnected framework members defining a plurality of cells. A portion of the interconnected framework members comprise a side branch structure that defines an inner side branch cell. The inner side branch cell is shaped differently from other cells of the stent. The side branch structure comprises a first serpentine ring, a second serpentine ring and a plurality of inner side branch connectors. The first serpentine ring extends around the inner side branch cell and comprises alternating inner turns and outer turns. The outer turns are aligned around a first reference circle. The second serpentine ring extends around the first serpentine ring and comprises alternating inner turns and outer turns. The inner turns are aligned around a second reference circle. Each inner side branch connector spans between the first serpentine ring and the second serpentine ring in a side branch radial direction. The first reference circle has a greater diameter than the second reference circle.

In at least one other embodiment, a stent comprises a plurality of interconnected framework members defining a plurality of cells. A portion of the interconnected framework members comprise a side branch structure defining an inner side branch cell that is shaped differently from other cells of the stent. The side branch structure comprises a first serpentine ring, a second serpentine ring and a plurality of side branch connectors. The first serpentine ring extends around the inner side branch cell and comprises alternating inner turns and outer turns. The second serpentine ring extends around the first serpentine ring and comprises alternating inner turns and outer turns. The second serpentine ring has the same number of outer turns as the first serpentine ring. Each side branch connector spans between the first serpentine ring and the second serpentine ring in a side branch radial direction.

In at least one other embodiment, a stent comprises a plurality of interconnected framework members defining a plurality of cells. A portion of the interconnected framework members comprise a side branch structure defining an inner side branch cell. The inner side branch cell is shaped differently from other cells of the stent. The side branch structure comprises a first serpentine ring, a second serpentine ring and a third serpentine ring. The first serpentine ring extends around the inner side branch cell and comprises alternating inner turns and outer turns. The outer turns are aligned around a first reference circle. The second serpentine ring extends around the first serpentine ring and comprises alternating inner turns and outer turns. The inner turns are aligned around a second reference circle and the outer turns are aligned around a third reference circle. The third serpentine ring extends around the second serpentine ring and comprises alternating inner turns and outer turns. The inner turns aligned are around a fourth reference circle. The first reference circle has a greater diameter than the second reference circle, and the third reference circle has a greater diameter than the fourth reference circle.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

FIGS. 2-6 each show a flat pattern for another embodiment of a stent.

Figure 6:
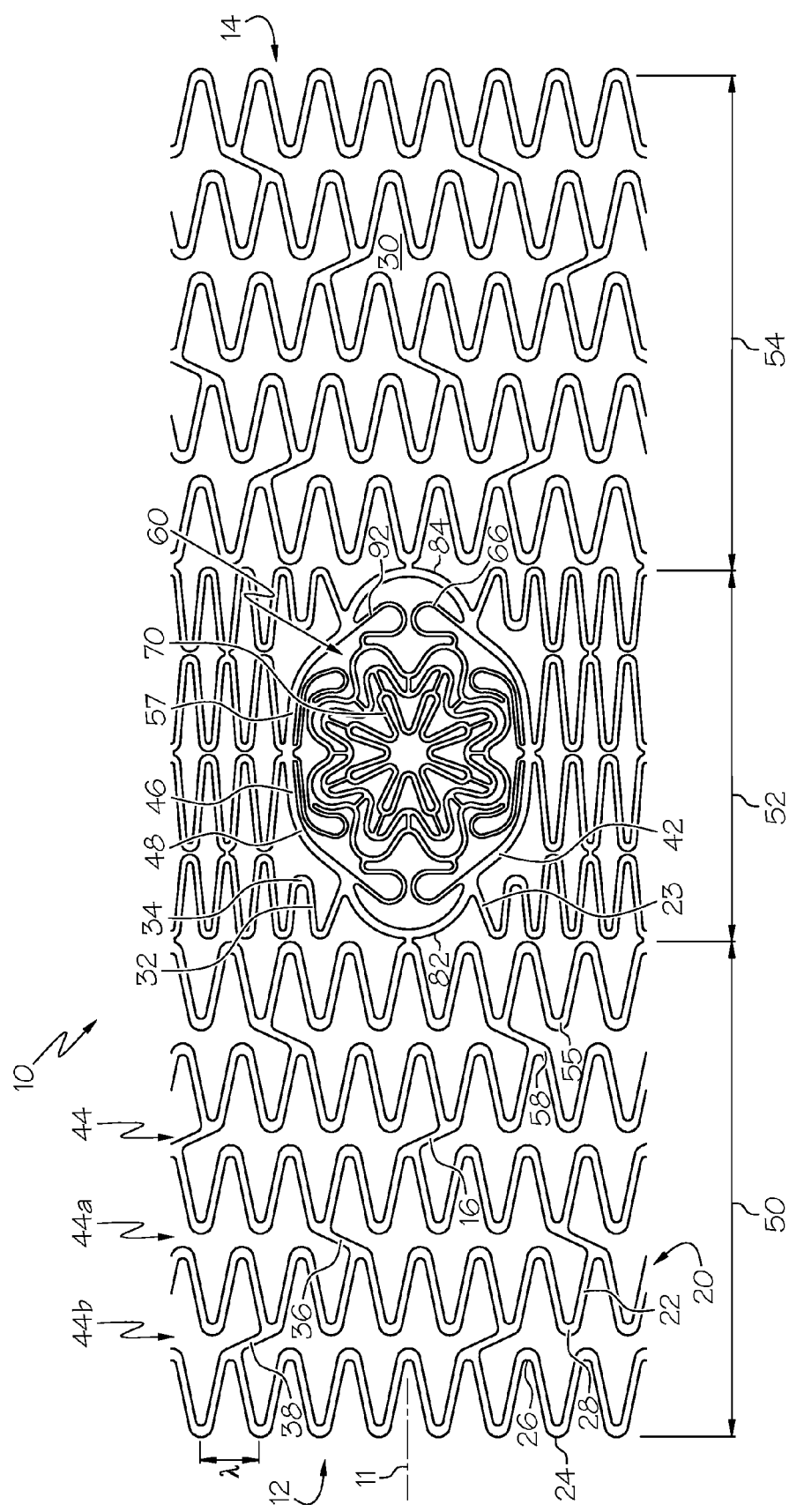
Figure 6A:
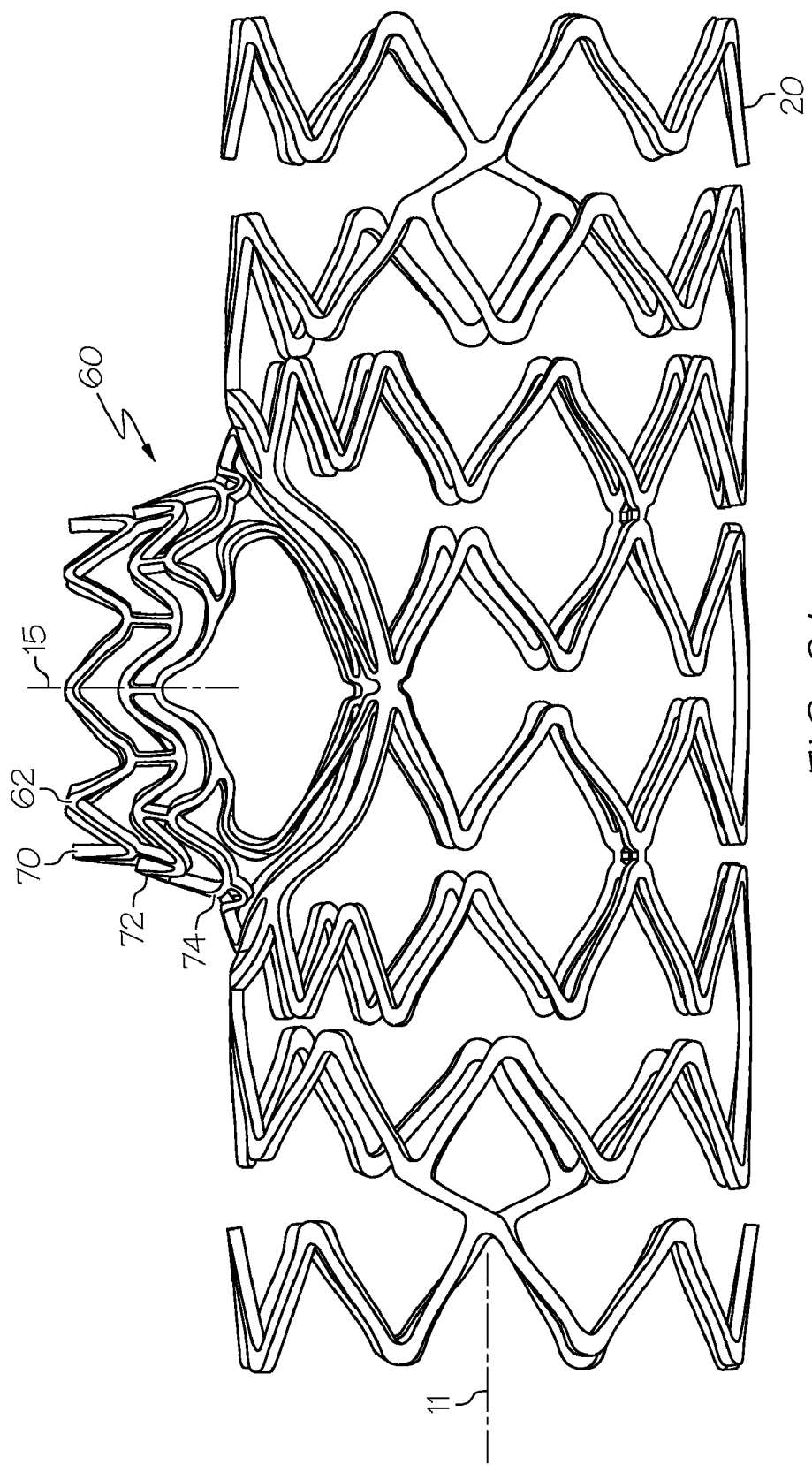

FIG. 6A shows a side view of an embodiment of a stent having a side branch structure similar to the side branch structure of the flat pattern shown in FIG. 6.

Figure 6B:
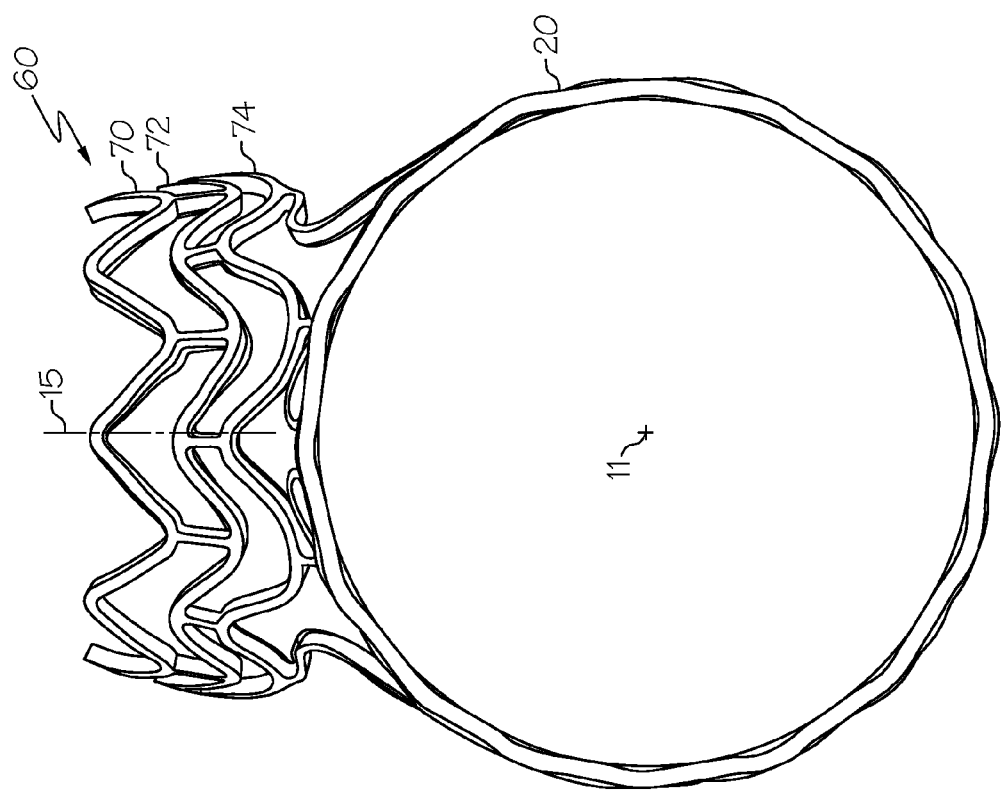

FIG. 6B shows an end view of the stent shown in FIG. 6A.

FIGS. 7-15 each show a flat pattern for another embodiment of a stent.

Figure 15:
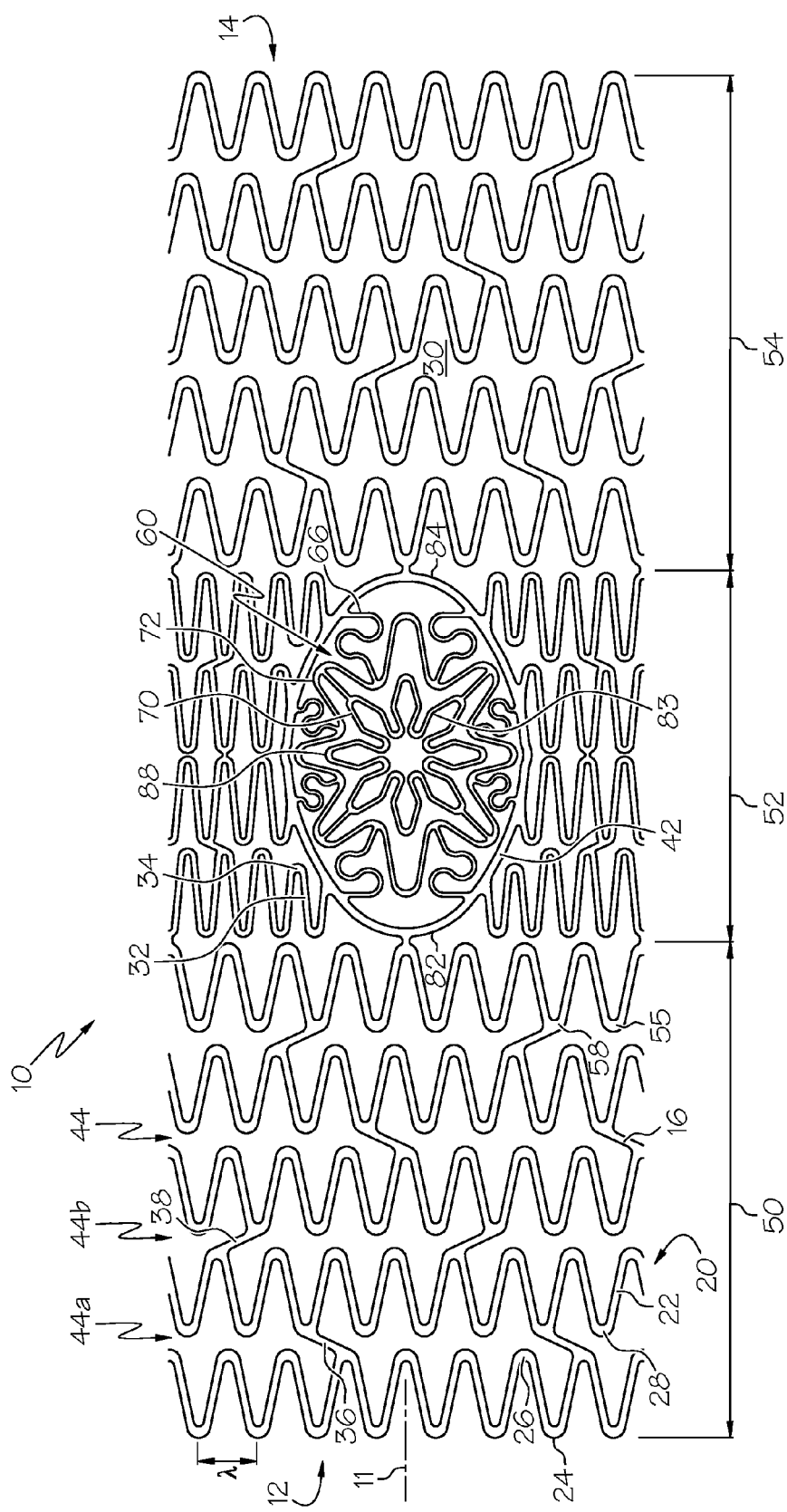
Figure 15A:
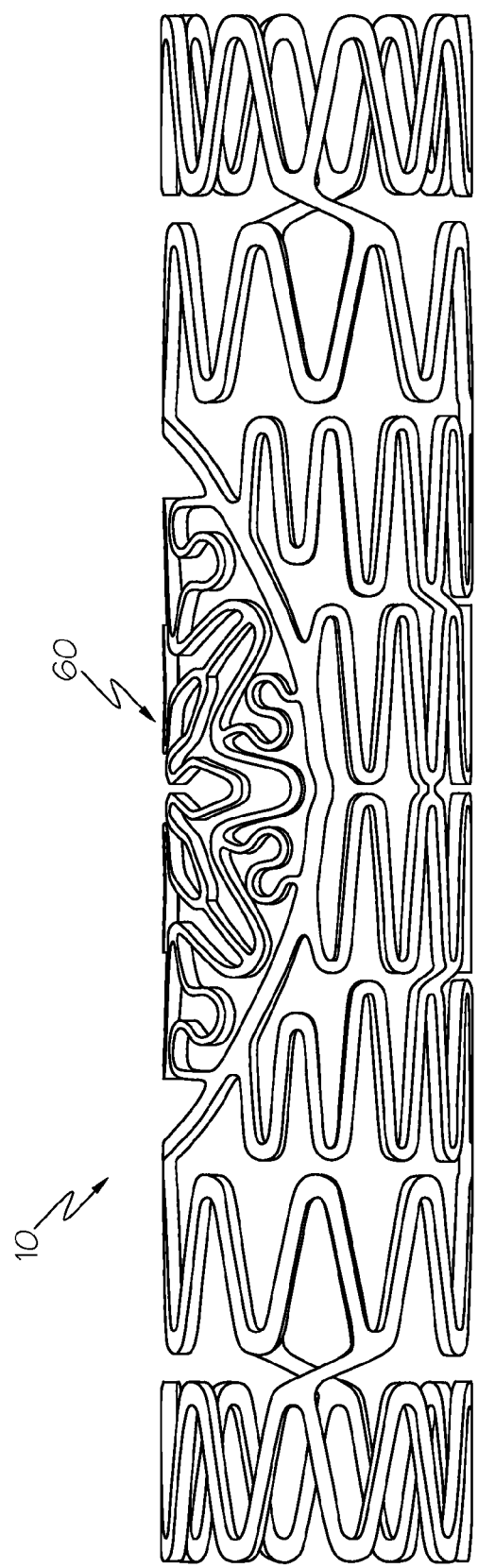

FIGS. 15A and 15B each show a side view of an embodiment of a stent having a side branch structure similar to the side branch structure of the flat pattern shown in FIG. 15.

Figure 15C:
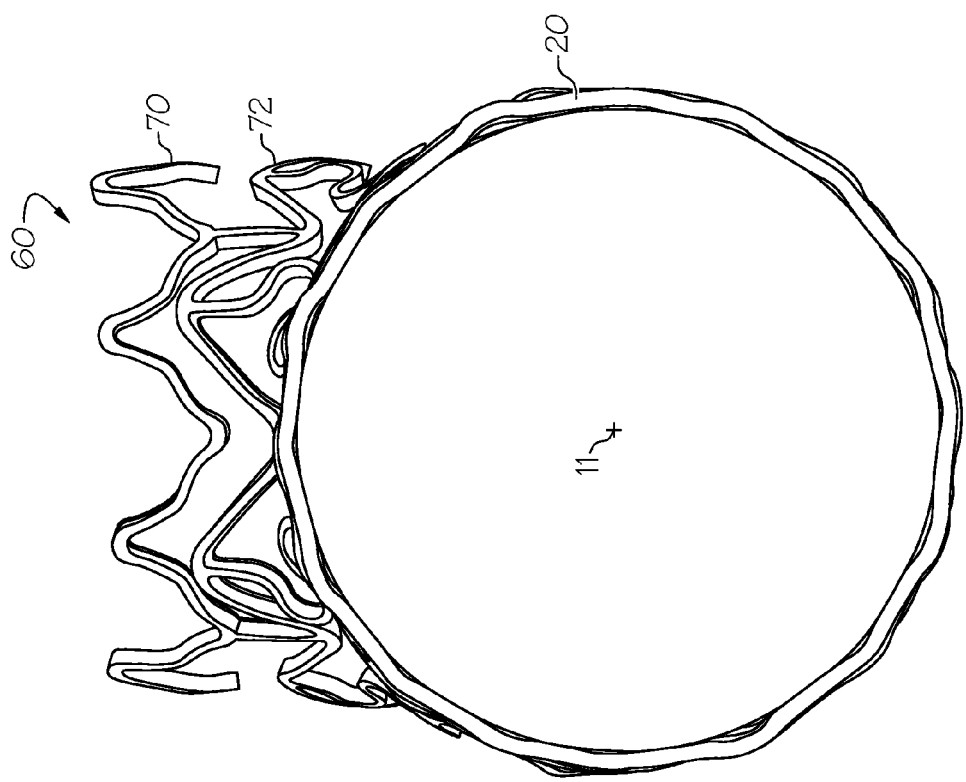

FIG. 15C shows an end view of the stent shown in FIG. 15B.

FIGS. 16-19 each show a flat pattern for another embodiment of a stent.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 1:
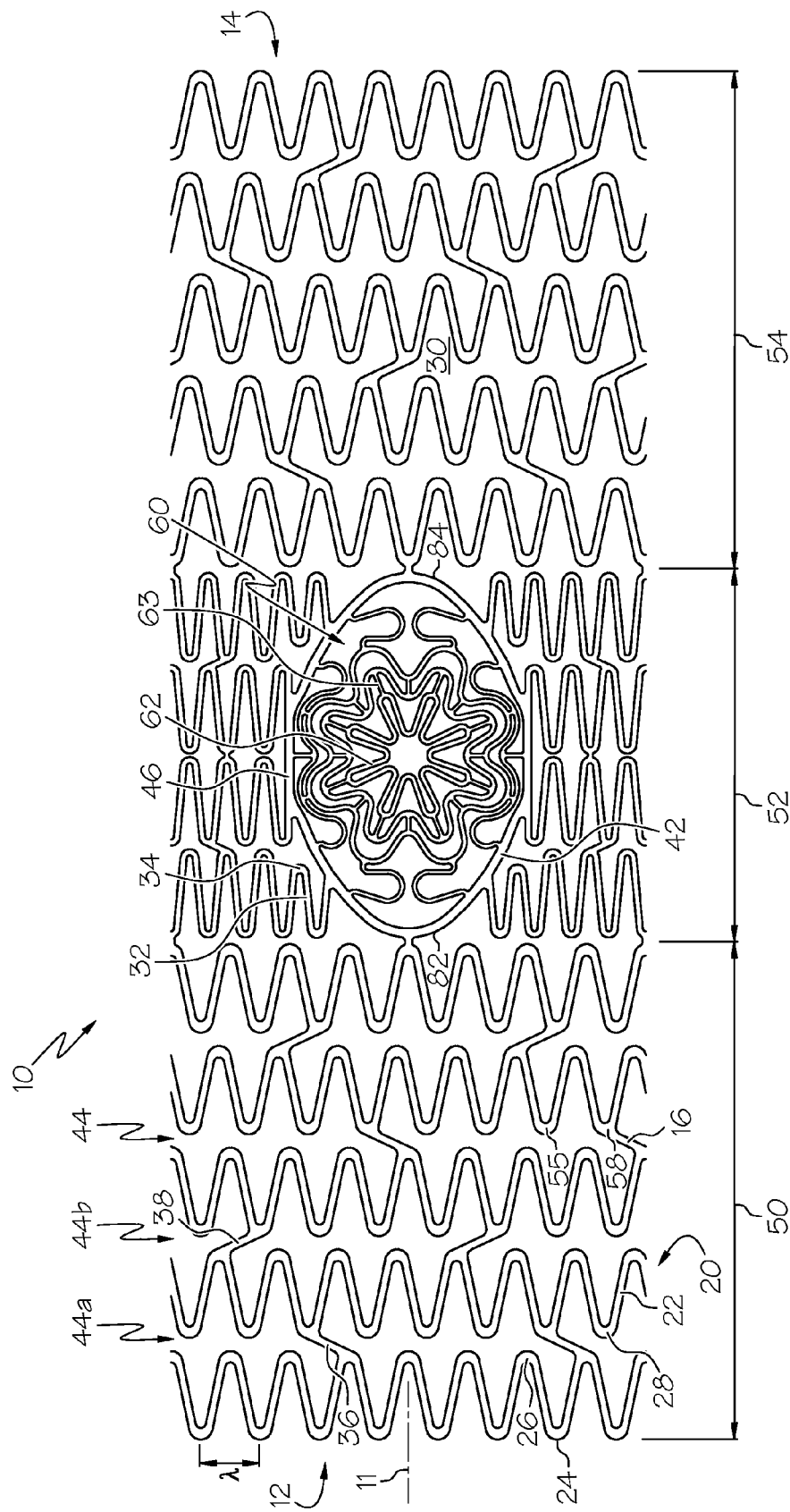
FIG. 1 shows a flat pattern for an embodiment of a stent.

FIG. 1 shows a flat pattern for an embodiment of a stent 10 having a proximal end 12, a distal end 14 and a plurality of serpentine bands 20. Each serpentine band 20 comprises a plurality of struts 22. Circumferentially adjacent struts 22 within a serpentine band 20 are connected by turns 28. Turns 28 that point toward the proximal end 12 of the stent 10 comprise proximal peaks 24, and turns 28 that point toward the distal end 14 of the stent 10 comprise distal valleys 26. Each serpentine band 20 extends about at least a portion of the circumference of the stent 10.

A stent 10 can have any suitable number of serpentine bands 20. In various embodiments, a serpentine band 20 can have any suitable number of struts 22 and any suitable number of turns 28. In some embodiments, a serpentine band 20 can have a constant wavelength λ or distance between repeating elements of the serpentine band 20. For example, a wavelength λ may comprise a distance between adjacent proximal peaks 24 of a serpentine band 20, or a distance between adjacent distal valleys 26 of a serpentine band 20. In some embodiments, the wavelength λ can change between adjacent serpentine bands 20. For example, the wavelength λ of various serpentine bands 20 may be the shortest for serpentine bands 20 located near the center of the stent 10, and may increase as the stent 10 is traversed toward either end 12, 14. In some embodiments, a serpentine band 20 may have multiple portions, where each portion comprises a different wavelength λ.

A serpentine band 20 can span any suitable distance along the length of the stent 10. In some embodiments, the proximal peaks 24 of a given serpentine band 20 can be aligned about a circumference of the stent 10, and the distal valleys 26 can be similarly aligned about another circumference of the stent 10. In some embodiments, various peaks 24 may be offset from other peaks 24 within a given serpentine band 20, and various valleys 26 may be offset from other valleys 26 within the band 20.

Each strut 22 comprises a width, which can be measured in a direction normal to the length of the strut 22. In some embodiments, all struts 22 within a given serpentine band 20 have the same width. In some embodiments, the width of various struts 22 within a serpentine band 20 can change. In some embodiments, the width of struts 22 of one serpentine band 20 can be different from the width of struts 22 of another serpentine band 20.

Each turn 28 has a width, which can be measured in a direction normal to the side of the turn 28 (i.e. normal to a tangent line). In some embodiments, the width of a turn 28 can be greater than the width of one or more struts 22 of the stent 10. In some embodiments, the width of a turn 28 may be less than the width of one or more struts 22 of the stent 10. In some embodiments, the width of a turn 28 may vary from one end of the turn 28 to the other. For example, a turn 28 may connect to a strut 22 at one end having the same width as the strut 22. The width of the turn 28 may increase, and in some embodiments may reach a maximum at a midpoint of the turn 28. The width of the turn 28 may then decrease to the width of another strut 22, which may be connected to the second end of the turn 28.

In some embodiments, serpentine bands 20 that are adjacent to one another along the length of the stent 10 are connected by at least one connector strut 16. In some embodiments, a connector strut 16 spans between turns 28 of adjacent serpentine bands 20. For example, one end of a connector strut 16 can connect to a distal valley 26 of one serpentine band 20, and the other end of the connector strut 16 can connect to a proximal peak 24 of an adjacent serpentine band 20.

Connector struts 16 can connect to any portion of a serpentine band 20, such as a turn 28, or in some embodiments, a strut 22. In some embodiments, a connector strut 16 is linear or straight along its length. In some embodiments, a connector strut 16 can include curvature along its length, can further include multiple portions of curvature, for example a convex portion and a concave portion that may be connected at an inflection point.

In some embodiments, a stent 10 comprises a first type of connector strut 36 and a second type of connector strut 38. A first connector strut 36 may extend in a first direction. The first connector strut 36 may be oriented at a first angle to a stent lengthwise axis 11. A second connector strut 38 may extend in a second direction that is different than or non-parallel to the first direction. In some embodiments, the first angle and the second angle may have the same magnitude but different orientations. For example, a first connector strut 36 may form a 70° angle with a stent lengthwise axis 11, while a second connector strut 38 may form a negative 70° angle with the stent lengthwise axis 11. In some embodiments, a first angle may comprise a mirror image of a second angle across a line parallel to the stent lengthwise axis 11.

A stent 10 further comprises a plurality of cells 30. A cell 30 comprises an opening in the stent 10 between the structural framework elements, such as serpentine bands 20 and connector struts 16. In some embodiments, a cell 30 may be bounded by a serpentine band 20, a connector strut 16, another serpentine band 20 and another connector strut 16.

In some embodiments, a stent 10 comprises a first end region 50, a central region 52 and a second end region 54. Each region 50, 52, 54 extends across a portion of the length of the stent 10. Each region 50, 52, 54 includes a plurality structural framework elements, for example a plurality of serpentine bands 20. In some embodiments, all of the serpentine bands 20 within a given region 50, 52, 54 are similar in size and shape. In some embodiments, various serpentine bands 20 within a given region 50, 52, 54 may be different in size, shape, strut width, wavelength $\lambda$, etc. For example, in some embodiments, serpentine bands 20 located in the central region 52 span a greater distance along the length of the stent 10 than serpentine bands 20 located in the end regions 50, 54. In some embodiments, the struts 22 of serpentine bands 20 located in the central region 52 have a greater length than struts 22 located in the end regions 50, 54. In some embodiments, the struts 22 of serpentine bands 20 located in the end regions 50, 54 are wider than struts 22 located in the central region 52. In some embodiments, the wavelength $\lambda$ of serpentine bands 20 located in the central region 52 is less than the wavelength $\lambda$ of serpentine bands 20 located in the end regions 50, 54.

In some embodiments, an area of the stent 10 located between two adjacent serpentine bands 20 can be considered a connector column 44. Each connector column 44 comprises a plurality of connector struts 16. In some embodiments, each connector strut 16 in a connector column 44 can be similar to one another. For example, each connector strut 16 in a first connector column 44a can comprise a first type of connector strut 36. Each connector strut 16 in a second connector column 44b can comprise a second type of connector strut 38.

In some embodiments, first connector columns 44a and second connector columns 44b can alternate along the length of the stent 10. Thus, each interior serpentine band 20 can be positioned between a first connector column 44a and a second connector column 44b. Accordingly, connector struts 16 that connect to one side of a serpentine band 20 can comprise first connector struts 36, and connector struts 16 that connect to the other side of the serpentine band 20 can comprise second connector struts 38.

Turns 28 can comprise connected turns 58 or unconnected turns 55 depending upon whether the turn 28 connects to a connector strut 16.

A serpentine band 20 can have more unconnected turns 55 than connected turns 58. In some embodiments, a serpentine band 20 has three unconnected turns 55 for each connected turn 58. The 3:1 ratio of unconnected turns 55 to connected turns 58 can also apply to the proximal peaks 24 and to the distal valleys 26.

In some embodiments, the central region 52 further comprises a side branch structure 60 and a side branch support ring 42. In various embodiments, some or all of the serpentine bands 20 located in the central region 52 extend about a portion of the stent circumference, while the remainder of the circumference is occupied by the side branch structure 60 and the support ring 42.

In some embodiments, serpentine bands 20 located in the central region 52 attach directly to a portion of the support ring 42.

In some embodiments, a serpentine band 20 comprises one or more shorter struts 32. A shorter strut 32 is generally shorter than other struts 22 of the serpentine band 20. Shorter struts 32 can be located in proximity to the side branch structure 60, and in some embodiments, a shorter strut 32 can connect to a portion of the side branch structure 60. A serpentine band 20 can also comprise one or more offset turns 34, which can connect to one or more shorter struts 32 and can further connect to the support ring 42. An offset turn 34 is generally offset from other turns 28 of the serpentine band 20 that face the same direction (e.g. point toward the same direction). For example, most of the distal valleys 26 of a serpentine band 20 may be aligned about a reference circumference of the stent 10, while an offset distal valley 34 located in the same serpentine band 20 is not aligned on the aforementioned reference circumference.

In various embodiments, serpentine bands 20 located in the central region 52 can comprise any suitable combination of struts 22 and turns 28, including struts of varying length, struts having curvature and turns having any suitable location and orientation.

The side branch structure 60 comprises structural elements that can displace outwardly from other portions of the stent 10, for example extending into a side branch vessel. The side branch structure 60 generally comprises a plurality of serpentine rings 62 and a plurality of side branch connectors 63.

Figure 1A:
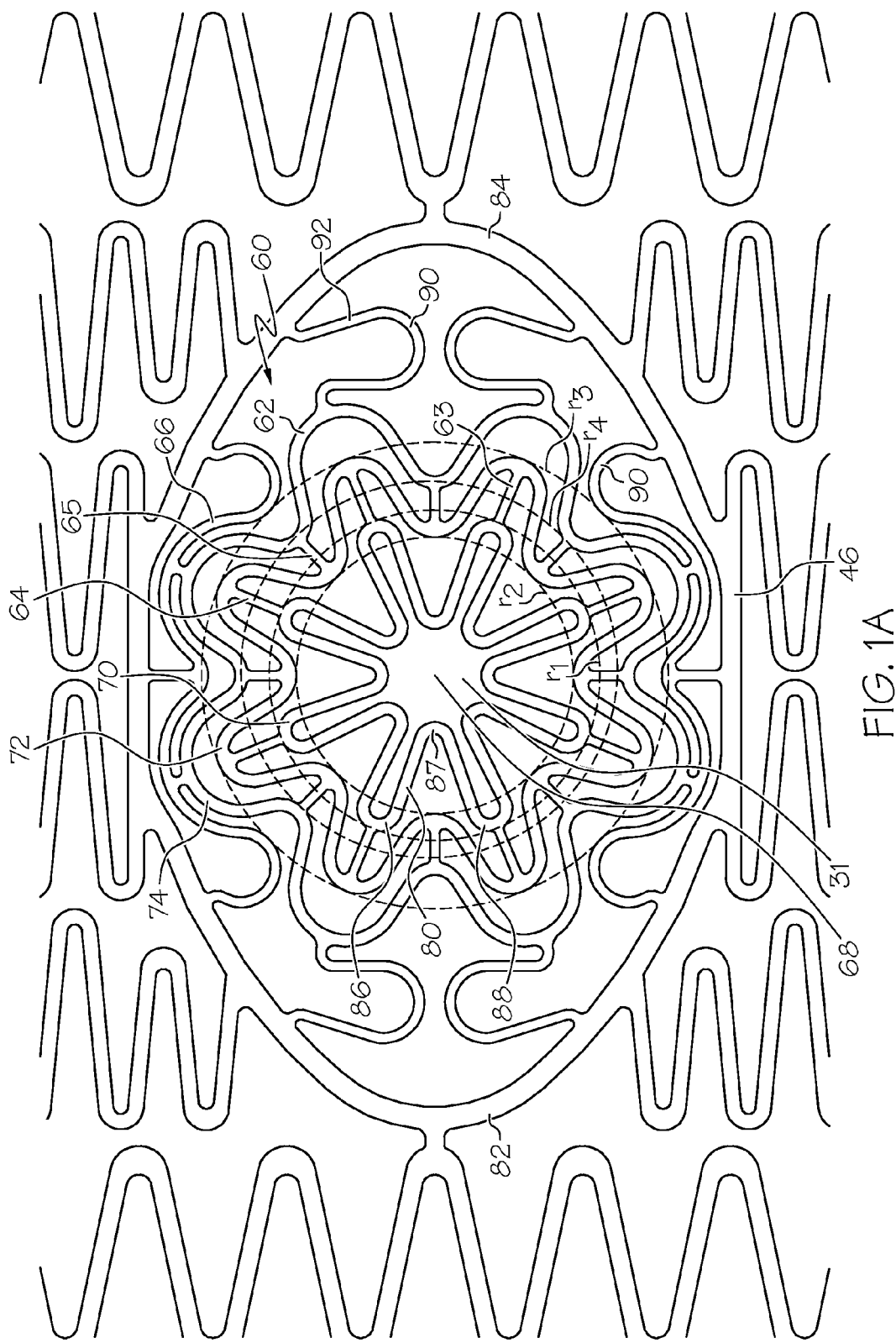
FIG. 1A shows a portion of FIG. 1 in greater detail.

FIG. 1A shows the side branch structure 60 from the embodiment of FIG. 1 in greater detail.

In some embodiments, the side branch structure 60 comprises a first serpentine ring 70, a second serpentine ring 72, a third serpentine ring 74, a plurality of side branch inner connectors 64, a plurality of side branch intermediate connectors 65 and a plurality of side branch outer connectors 66. The serpentine rings can also be referred to herein as side branch rings. In some embodiments, the first serpentine ring 70 comprises an inner serpentine ring, the second serpentine ring 72 comprises an intermediate serpentine ring and the third serpentine ring 74 comprises an outer serpentine ring.

The first serpentine ring 70 extends around and defines an inner side branch cell 31. The inner side branch cell 31 can be shaped differently from all other cells 30 of the stent 10. A side branch center point 68 comprises the center of the inner side branch cell 31. In some embodiments, the side branch rings 70, 72, 74 are centered upon the side branch center point 68.

In some embodiments, the first serpentine ring 70 comprises a plurality of alternating struts 80 and turns 86. In some embodiments, each strut 80 is straight along its length. In some embodiments, each strut 80 of the first serpentine ring 70 has the same length.

In some embodiments, the first serpentine ring 70 can be symmetrical across a side branch major axis that extends parallel to the stent longitudinal axis 11. In some embodiments, the first serpentine ring 70 can be symmetrical across a side branch minor axis that extends perpendicular to the stent longitudinal axis 11.

In some embodiments, a turn 86 can be centered in a side branch radial direction. Thus, a line oriented in a side branch radial direction that passes through the side branch center point 68 can bisect a turn 86.

In some embodiments, the turns 86 of the first serpentine ring 70 comprise alternating inner turns 87 and outer turns 88. Thus, the turns 86 located on either side of an inner turn 87 comprise outer turns 88, and the turns 86 located on either side of an outer turn 88 comprise inner turns 87. The inner turns 87 are generally located closer to the side branch center point 68 than the outer turns 88. In some embodiments, inner turns 87 point inward with respect to the side branch, for example pointing toward the side branch center point 68. In some embodiments, outer turns 88 point outward with respect to the side branch, for example pointing away from the side branch center point 68.

In some embodiments, each inner turn 87 of the first serpentine ring 70 comprises the same shape and has the same radius of curvature as all other inner turns 87 of the first serpentine ring 70. In some embodiments, each outer turn 88 of the first serpentine ring 70 comprises the same shape and has the same radius of curvature as all other outer turns 88 of the first serpentine ring 70.

In some embodiments, the outer turns 88 of the first serpentine ring 70 are each located an equal distance away from the side branch center point 68, and thus can be considered aligned around a first reference circle $r_1$ centered upon the side branch center point 68. In some embodiments, the outer turns 88 of the first serpentine ring 70 are equally spaced around the first reference circle $r_1$.

The second serpentine ring 72 extends around the first serpentine ring 70. In some embodiments, the second serpentine ring 72 is coaxial with the first serpentine ring 70, and thus can be centered upon the side branch center point 68.

In some embodiments, the second serpentine ring 72 comprises a plurality of alternating struts 80 and turns 86. In some embodiments, each strut 80 is straight along its length. In some embodiments, each strut 80 of the second serpentine ring 72 has the same length. In some embodiments, struts 80 of the second serpentine ring 72 are shorter than struts 80 of the first serpentine ring 70.

In some embodiments, the turns 86 of the second serpentine ring 72 comprise alternating inner turns 87 and outer turns 88. Thus, the turns 86 located on either side of an inner turn 87 comprise outer turns 88, and the turns 86 located on either side of an outer turn 88 comprise inner turns 87. The inner turns 87 are generally located closer to the side branch center point 68 than the outer turns 88. In some embodiments, inner turns 87 point inward with respect to the side branch, for example pointing toward the side branch center point 68. In some embodiments, outer turns 88 point outward with respect to the side branch, for example pointing away from the side branch center point 68.

In some embodiments, the second serpentine ring 72 can comprise the same number of struts 80 and turns 86 as the first serpentine ring 70. In some embodiments, the second serpentine ring 72 can comprise the same number of inner turns 87 and outer turns 88 as the first serpentine ring 70.

In some embodiments, the second serpentine ring 72 can be symmetrical across a side branch major axis that extends parallel to the stent longitudinal axis 11. In some embodiments, the second serpentine ring 72 can be symmetrical across a side branch minor axis that extends perpendicular to the stent longitudinal axis 11.

In some embodiments, a turn 86 of the second serpentine ring 72 can be centered in a side branch radial direction. Thus, a line oriented in a side branch radial direction that passes through the side branch center point 68 can bisect a turn 86.

In some embodiments, a turn 86 of the second serpentine ring 72 can be aligned with a turn 86 of the first serpentine ring 70 in a side branch radial direction. Thus, a line oriented in a side branch radial direction that bisects a turn 86 of the first serpentine ring 70 can also bisect a turn 86 of the second serpentine ring 72. When a turn 86 is bisected by a line, a first half of the turn located on one side of the line comprises a mirror image of a second half of the turn located on the other side of the line. In some embodiments, an inner turn 87 of the second serpentine ring 72 can be aligned with an inner turn 87 of the first serpentine ring 70 in a side branch radial direction. In some embodiments, an outer turn 88 of the second serpentine ring 72 can be aligned with an outer turn 88 of the first serpentine ring 70 in a side branch radial direction.

In some embodiments, each inner turn 87 of the second serpentine ring 72 comprises the same shape and has the same radius of curvature as all other inner turns 87 of the second serpentine ring 72. In some embodiments, each outer turn 88 of the second serpentine ring 72 comprises the same shape and has the same radius of curvature as all other outer turns 88 of the second serpentine ring 72.

In some embodiments, the inner turns 87 of the second serpentine ring 72 are each located an equal distance away from the side branch center point 68, and thus can be considered aligned around a second reference circle $r_2$ centered upon the side branch center point 68. In some embodiments, the inner turns 87 of the second serpentine ring 72 are equally spaced around the second reference circle $r_2$.

In some embodiments, the outer turns 88 of the first serpentine ring 70 can be located farther away from the side branch center point 68 than the inner turns 87 of the second serpentine ring 72. Thus, the second reference circle $r_2$ can have a smaller diameter than the first reference circle $r_1$.

In some embodiments, an inner connector 64 connects between the first serpentine ring 70 and the second serpentine ring 72. In some embodiments, an inner connector 64 is connected at an inner end to a turn 86 of the first side branch ring 70 and is connected at an outer end to a turn 86 of the second side branch ring 72. In some embodiments, an inner connector 64 spans between an outer turn 88 of the first serpentine ring 70 and an outer turn 88 of the second serpentine ring 72.

In some embodiments, an inner connector 64 is straight along its length and is oriented in a side branch radial direction. In some embodiments, one inner connector 64 and another inner connector 64 that is located across the inner side branch cell 31 are both oriented upon a common reference line that passes through the side branch center point 68. In some embodiments, all of the inner connectors 64 are evenly distributed around the side branch center point 68.

In some embodiments, the number of inner connectors 64 is equal to the number of outer turns 88 of the first serpentine ring 70.

The third serpentine ring 74 extends around the second side branch ring 70. In some embodiments, the third serpentine ring 74 is coaxial with the second serpentine ring 72, and thus can be centered upon the side branch center point 68.

In some embodiments, the third serpentine ring 74 comprises a plurality of alternating struts 80 and turns 86. In some embodiments, each strut 80 is straight along its length.

In some embodiments, the turns 86 of the third serpentine ring 74 comprise alternating inner turns 87 and outer turns 88. Thus, the turns 86 located on either side of an inner turn 87 comprise outer turns 88, and the turns 86 located on either side of an outer turn 88 comprise inner turns 87. The inner turns 87 are generally located closer to the side branch center point 68 than the outer turns 88. In some embodiments, inner turns 87 point inward with respect to the side branch, for example pointing toward the side branch center point 68. In some embodiments, outer turns 88 point outward with respect to the side branch, for example pointing away from the side branch center point 68.

In some embodiments, the third serpentine ring 74 can comprise the same number of struts 80 and turns 86 as the second serpentine ring 72. In some embodiments, the third serpentine ring 74 can comprise the same number of inner turns 87 and outer turns 88 as the second serpentine ring 72.

In some embodiments, the third serpentine ring 74 can comprise the same number of struts 80 and turns 86 as the first serpentine ring 70. In some embodiments, the third serpentine ring 74 can comprise the same number of inner turns 87 and outer turns 88 as the first serpentine ring 70.

In some embodiments, the third serpentine ring 72 can be symmetrical across a side branch major axis that extends parallel to the stent longitudinal axis 11. In some embodiments, the third serpentine ring 74 can be symmetrical across a side branch minor axis that extends perpendicular to the stent longitudinal axis 11.

In some embodiments, a turn 86 of the third serpentine ring 74 can be centered in a side branch radial direction. Thus, a line oriented in a side branch radial direction that passes through the side branch center point 68 can bisect a turn 86.

In some embodiments, a turn 86 of the third serpentine ring 74 can be aligned with a turn 86 of the second serpentine ring 72 in a side branch radial direction. Thus, a line oriented in a side branch radial direction that bisects a turn 86 of the second serpentine ring 72 can also bisect a turn 86 of the third serpentine ring 74. In some embodiments, an inner turn 87 of the third serpentine ring 74 can be aligned with an inner turn 87 of the second serpentine ring 72 in a side branch radial direction. In some embodiments, an outer turn 88 of the third serpentine ring 74 can be aligned with an outer turn 88 of the second serpentine ring 72 in a side branch radial direction.

In some embodiments, a line oriented in a side branch radial direction can bisect inner turns 87 of the first, second and third serpentine rings 70, 72, 74. In some embodiments, a line oriented in a side branch radial direction can bisect outer turns 88 of the first, second and third serpentine rings 70, 72, 74.

In some embodiments, each inner turn 87 of the third serpentine ring 74 comprises the same shape and has the same radius of curvature as all other inner turns 87 of the third serpentine ring 74. In some embodiments, each outer turn 88 of the third serpentine ring 74 comprises the same shape and has the same radius of curvature as all other outer turns 88 of the third serpentine ring 74.

In some embodiments, the outer turns 88 of the second serpentine ring 72 are each located an equal distance away from the side branch center point 68, and thus can be considered aligned around a third reference circle $r_3$ centered upon the side branch center point 68. In some embodiments, the outer turns 88 of the second serpentine ring 72 are equally spaced around the third reference circle $r_3$.

In some embodiments, the inner turns 87 of the third serpentine ring 74 are each located an equal distance away from the side branch center point 68, and thus can be considered aligned around a fourth reference circle $r_4$ centered upon the side branch center point 68. In some embodiments, the inner turns 87 of the third serpentine ring 74 are equally spaced around the fourth reference circle $r_4$.

In some embodiments, the outer turns 88 of the second serpentine ring 72 can be located farther away from the side branch center point 68 than the inner turns 87 of the third serpentine ring 74. Thus, the fourth reference circle $r_4$ can have a smaller diameter than the third reference circle $r_3$.

In some embodiments, an intermediate connector 66 connects between the second serpentine ring 72 and the third serpentine ring 74. In some embodiments, an intermediate connector 66 is connected at an inner end to a turn 86 of the second serpentine ring 72 and is connected at an outer end to a turn 86 of the third serpentine ring 74. In some embodiments, an intermediate connector 66 spans between an inner turn 87 of the second serpentine ring 72 and an inner turn 87 of the third serpentine ring 74.

In some embodiments, an intermediate connector 66 is straight along its length and is oriented in a side branch radial direction. In some embodiments, one intermediate connector 66 and another intermediate connector 66 that is located across the inner side branch cell 31 are both oriented upon a common reference line that passes through the side branch center point 68. In some embodiments, all of the intermediate connector 66 are evenly distributed around the side branch center point 68.

In some embodiments, the number of intermediate connectors 66 is equal to the number of inner turns 87 of the second serpentine ring 72.

In some embodiments, a side branch outer connector 66 connects between the third serpentine ring 74 and the support ring 42. In some embodiments, a side branch outer connector 66 comprises at least one curved portion 90 and at least one straight portion 92. In some embodiments, a side branch outer connector 66 comprises a plurality of curved portions 90 connected by an inflection point where the curvature reverses orientation.

In some embodiments, a side branch outer connector 66 is connected at one end to the third serpentine ring 74 and is connected at the other end to the support ring 42.

In some embodiments, a side branch outer connector 66 is connected at each end to the support ring 42, and is connected to the third serpentine ring 74 at one or more locations along its length.

In some embodiments, each outer turn 88 of the third serpentine ring 74 is connected to a side branch outer connector 66.

The support ring 42 extends around the side branch structure 60 and provides a more rigid support to the side branch structure 60 than would otherwise be provided by the serpentine bands 20 alone. In some embodiments, the support ring 42 comprises a substantially constant strut width, and in some embodiments, struts of the support ring 42 have a greater width than elements of the serpentine bands 20 or other side branch structure 60.

In some embodiments, the support ring 42 extends continuously around the side branch structure 60. In some embodiments, the support ring 42 comprises a structure that is continuously concave with respect to the side branch center point 68. Thus, in some embodiments, the support ring 42 does not include any portions of curvature that are convex with respect to the side branch center point 68.

In some embodiments, the support ring 42 includes a first portion 82 and a second portion 84 located on axially opposed sides of the side branch structure 60. In some embodiments, the second portion 84 comprises a mirror image of the first portion taken across the side branch minor axis, which can be oriented in a stent circumferential direction and can pass through the side branch center point 68. In some embodiments, at least a portion of either portion 82, 84 can comprise a parabolic shape that is concave with respect to the side branch center point 68.

In some embodiments, the support ring 42 comprises at least one straight portion 46. In some embodiments, a straight portion 46 is oriented parallel to the stent longitudinal axis 11.

Figure 2:
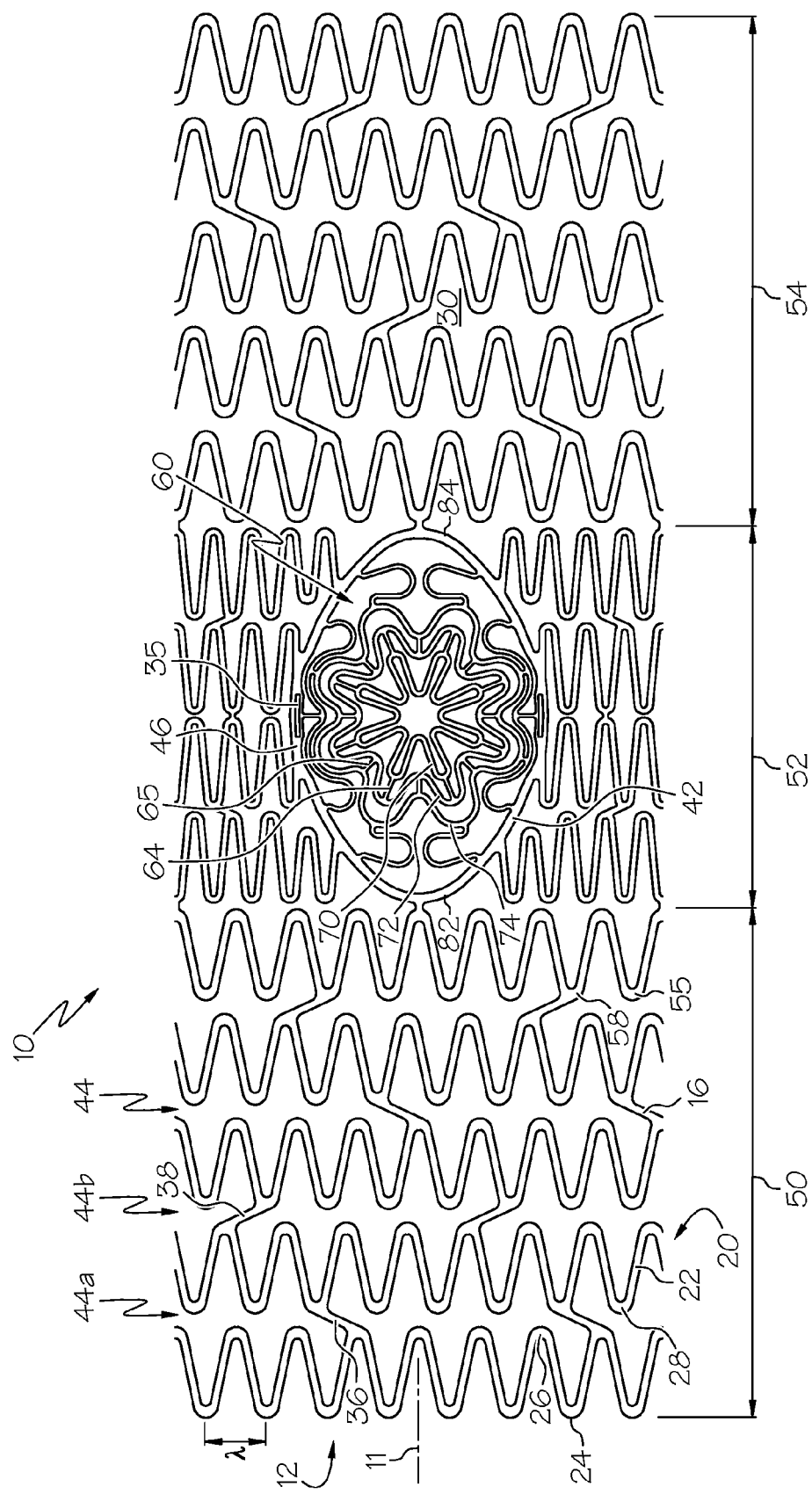

FIG. 2 shows a flat pattern for another embodiment of a stent 10.

In some embodiments, the support ring 42 comprises a support ring cell 35 that is contained within the width of the support ring 42. In some embodiments, a support ring cell 35 comprises an aperture in a straight portion 46.

Figure 3:
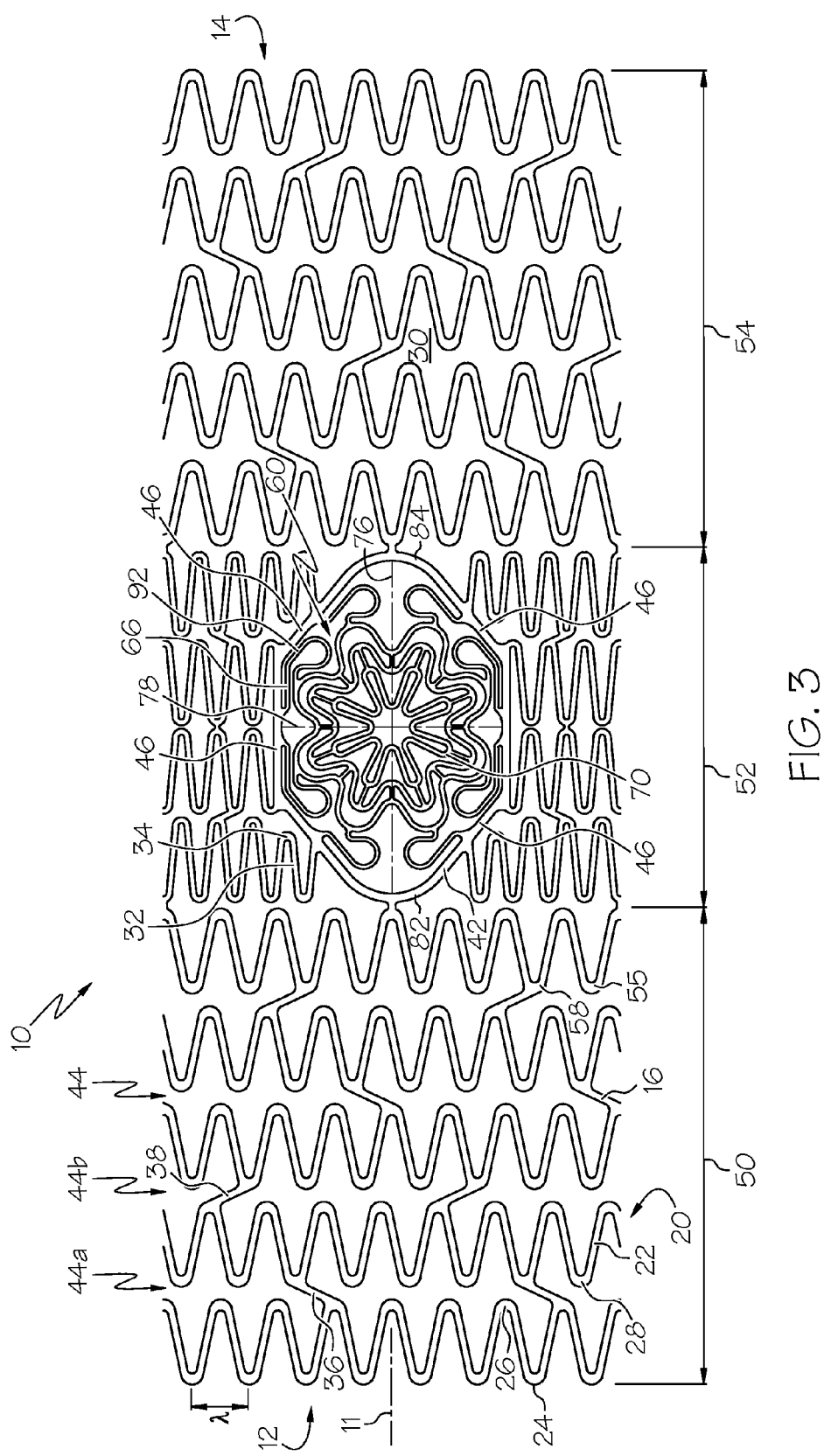

FIG. 3 shows a flat pattern for another embodiment of a stent 10.

In some embodiments, the support ring 42 comprises a plurality of straight portions 46 that are oriented at a non-zero angle to the stent longitudinal axis 11. In some embodiments, multiple straight portions 46 can comprise mirror images of one another taken across the side branch major axis 76 or the side branch minor axis 78.

In some embodiments, a side branch outer connector 66 comprises a straight portion 92 that is directly adjacent to and parallel to a straight portion 46 of the support ring 42. In some embodiments, a side branch outer connector 66 comprises multiple straight portions 92 that are nonparallel to one another, wherein each straight portion 92 is directly adjacent to and parallel to a respective straight portion 46 of the support ring 42.

In some embodiments, a side branch outer connector 66 and a serpentine band 20 can connect to opposite sides of a single location along the length of the support ring 42.

Figure 4:
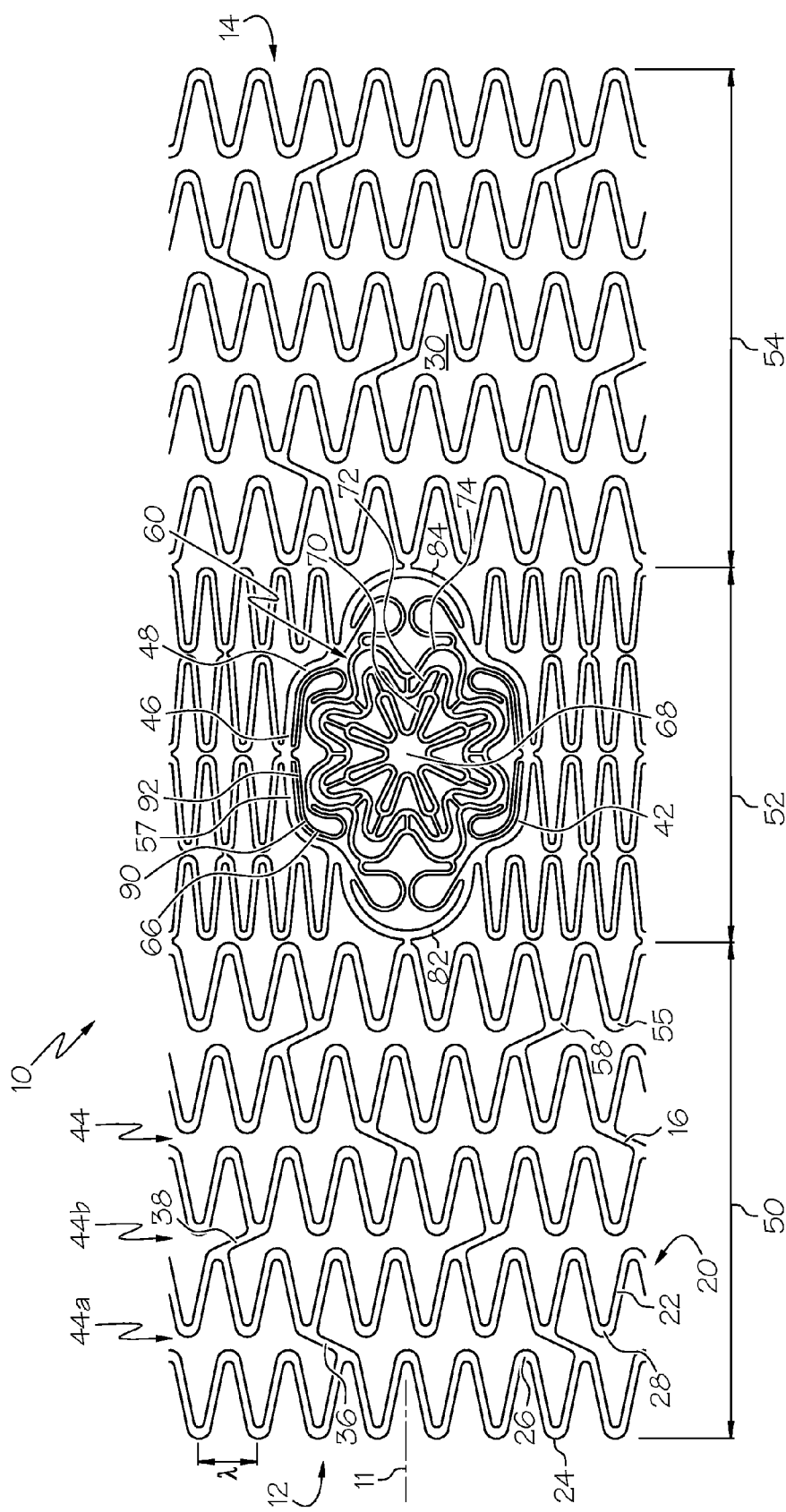

FIG. 4 shows a flat pattern for another embodiment of a stent 10.

In some embodiments, a support ring 42 comprises a plurality of straight portions 46 and a plurality of curved portions 48. In some embodiments, a curved portion 48 can be convex with respect to the side branch center point 68. In some embodiments, a curved portion 48 can be concave with respect to the side branch center point 68. In some embodiments of a support ring 42, the orientations of adjacent curved portions 48 can alternate between convex and concave as the support ring 42 is traversed around its perimeter.

In some embodiments, the support ring 42 comprises at least one continuation strut 57 that comprises a continuation of a serpentine band 20. Thus, the support ring 42 at least partially transitions into the serpentine band 20 via the continuation strut 57. A continuation strut 57 is connected to a serpentine band 20 and is also connected to a portion of the support ring 42, such as a curved portion 42 and/or another continuation strut 57.

Each continuation strut 57 can be substantially straight along its length. In some embodiments, a continuation strut 57 is oriented parallel to a plurality of struts 22 of the serpentine band 20 to which it connects.

In some embodiments, a continuation strut 57 has a greater width than the struts 22 the serpentine band 20 to which it is attached. In some embodiments, a continuation strut 57 comprises the same width as other portions of the support ring 442.

In some embodiments, a side branch outer connector 66 comprises a curved portion 90 that is directly adjacent to and substantially parallel along its length to a curved portion 48 of the support ring 42. In some embodiments, the side branch outer connector 66 can further comprise a straight portion 92 that is directly adjacent to and parallel to a straight portion 46 of the support ring 42. In some embodiments, the side branch outer connector 66 can comprise a straight portion 92 that is directly adjacent to and parallel to a continuation strut 57 of the support ring 42.

Figure 5:
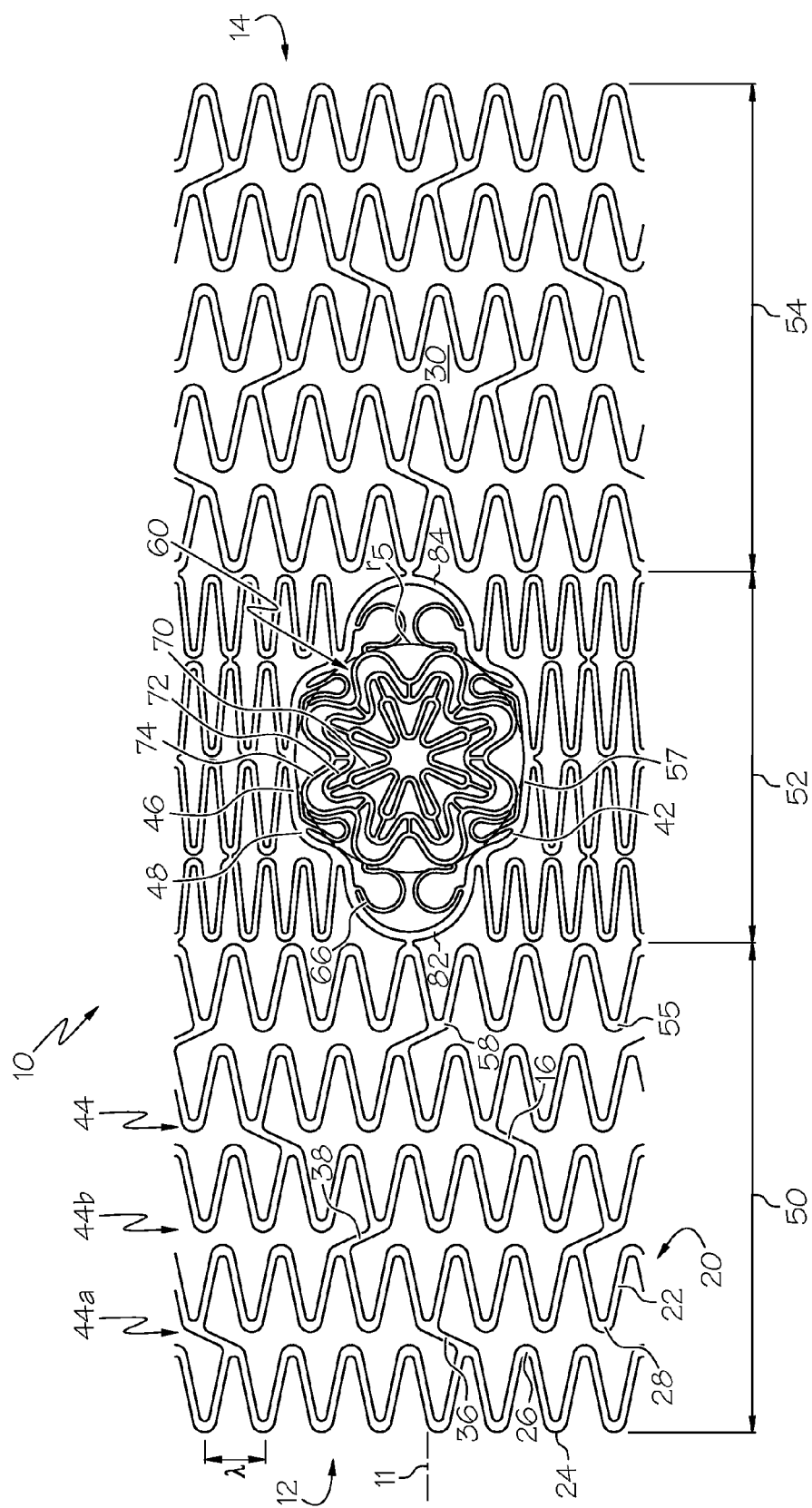

FIG. 5 shows a flat pattern for another embodiment of a stent 10.

In some embodiments, the outer turns 88 of the third serpentine ring 74 are each located an equal distance away from the side branch center point 68, and thus can be considered aligned around a fifth reference circle $r_5$ centered upon the side branch center point 68. In some embodiments, the outer turns 88 of the third serpentine ring 74 are equally spaced around the fifth reference circle $r_5$.

In some embodiments, the radial spacing between an outer turn 88 of the second serpentine ring 72 and a radially aligned outer turn 88 of the third serpentine ring 74 is constant for all pairs of radially aligned outer turns 88 between the second serpentine ring 72 and the third serpentine ring 74.

FIG. 6 shows a flat pattern for another embodiment of a stent 10 comprising another embodiment of a support ring 42 and further embodiments of side branch outer connectors 66.

In some embodiments, a straight portion 46 of the support ring 42 transitions into a straight portion 92 of a side branch outer connector 66, wherein the two straight portions 46, 92 are parallel and, in some embodiments, comprise a continuous surface that is oriented in a stent radial direction.

In some embodiments, an offset turn 34 of a serpentine band 20, for example a serpentine band 20 located in the central region 52 of the stent 10, can comprise a greater width than other turns 28 of the serpentine band 20.

In some embodiments, a serpentine band 20 can comprise one or more nonparallel struts 23, wherein the nonparallel strut 23 is not parallel to any other struts 22 of the serpentine band 20 when viewed as a flat pattern.

FIG. 6A shows a three-dimensional view of an embodiment of a stent 10 having a side branch structure 60 similar to the side branch structure 60 shown the pattern of FIG. 6. The stent 10 is shown in an expanded configuration with the side branch structure 60 outwardly deployed.

The serpentine bands 20 form a generally cylindrical stent body structure that extends around the stent longitudinal axis 11. The side branch structure 60 extends in a radial outward direction above the generally cylindrical stent body structure. Portions of the outwardly deployed side branch structure 60 are located farther away from the stent longitudinal axis 11 than portions of the stent 10 that form the generally cylindrical stent body structure.

The outwardly deployed side branch rings 62 form a tubular structure having a side branch axis 15 that is nonparallel to the stent longitudinal axis 11. In some embodiments, the side branch axis 15 is orthogonal to the stent longitudinal axis 11.

FIG. 6B shows an end view of the stent 10 shown in FIG. 6A.

Figure 7:
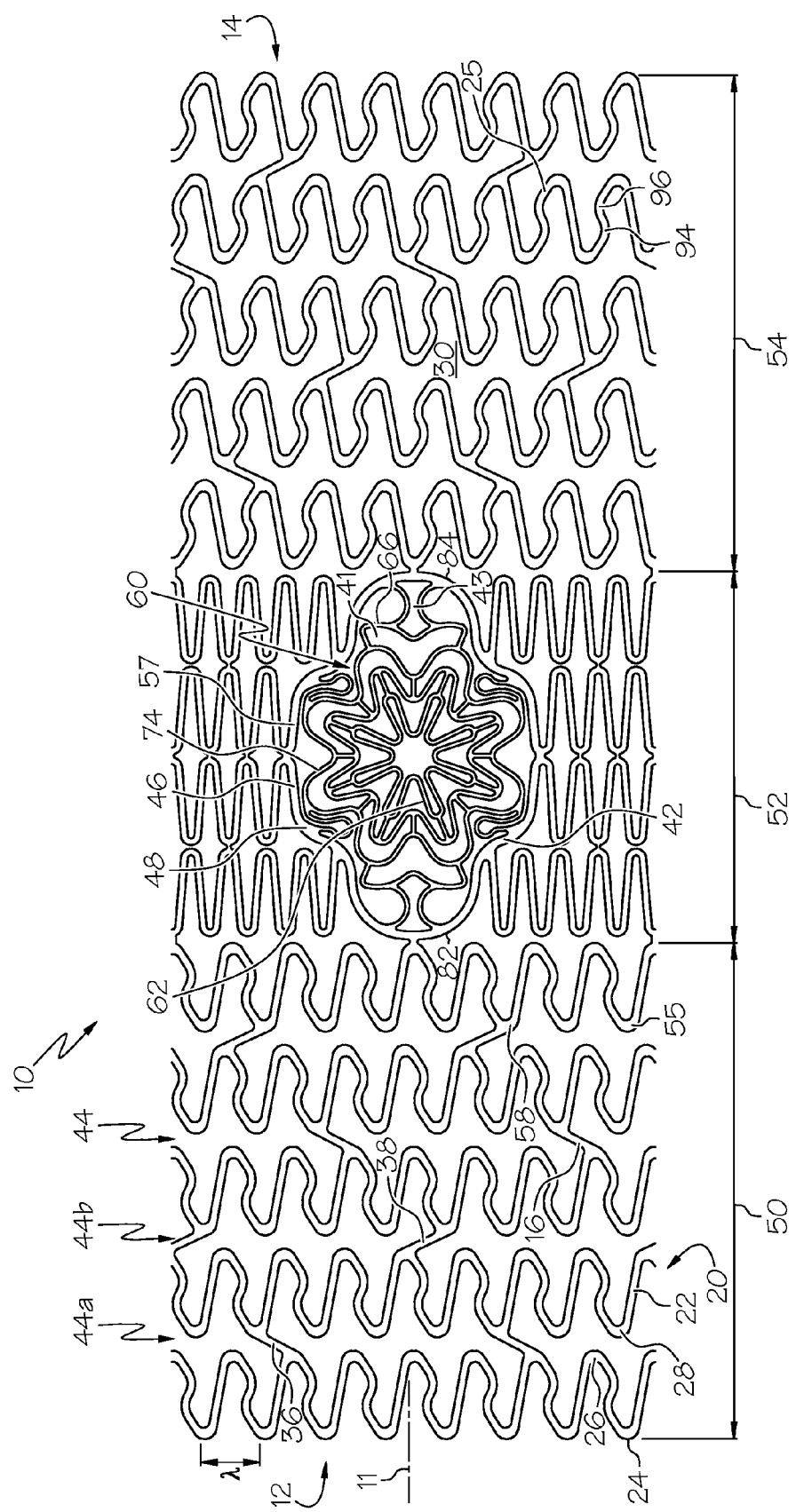

FIG. 7 shows a flat pattern for another embodiment of a stent 10 comprising another embodiment of a support ring 42 and further embodiments of side branch outer connectors 66.

In some embodiments, a stent 10 comprises a cell 41 that is bounded only by a side branch ring 62 and one or more side branch outer connectors 66. In some embodiments, a stent 10 comprises a cell 41 that is bounded only by the third serpentine ring 74 and one or more side branch outer connectors 66.

In some embodiments, a stent 10 comprises a cell 43 that is bounded only by the support ring 42 and one or more side branch outer connectors 66.

In some embodiments, a serpentine band 20 can comprise one or more bent struts 25. In some embodiments, a bent strut 25 comprises an s-shape. In some embodiments, an s-shape comprises a first curved portion 94 and a second curved portion 96. The curvature orientation of the first curved portion 94 is different from the curvature orientation of the second curved portion 96. For example, if the first curved portion 94 can considered convex, the second curved portion 96 can be considered concave. An s-shaped strut 25 can include an inflection point where the curvature changes orientation.

In some embodiments, a serpentine band 20 comprises alternating straight struts 22 and bent or s-shaped struts 25.

In some embodiments, a stent 10 comprises at least one serpentine band 20 that includes bent struts 25 and at least one serpentine band 20 wherein all of the struts 22 are straight. In some embodiments, all of the serpentine bands 20 in either end portion 50, 54 comprise bent struts 25, and all of the struts 22 of the serpentine bands 20 in the central region 52 are straight.

Figure 8:
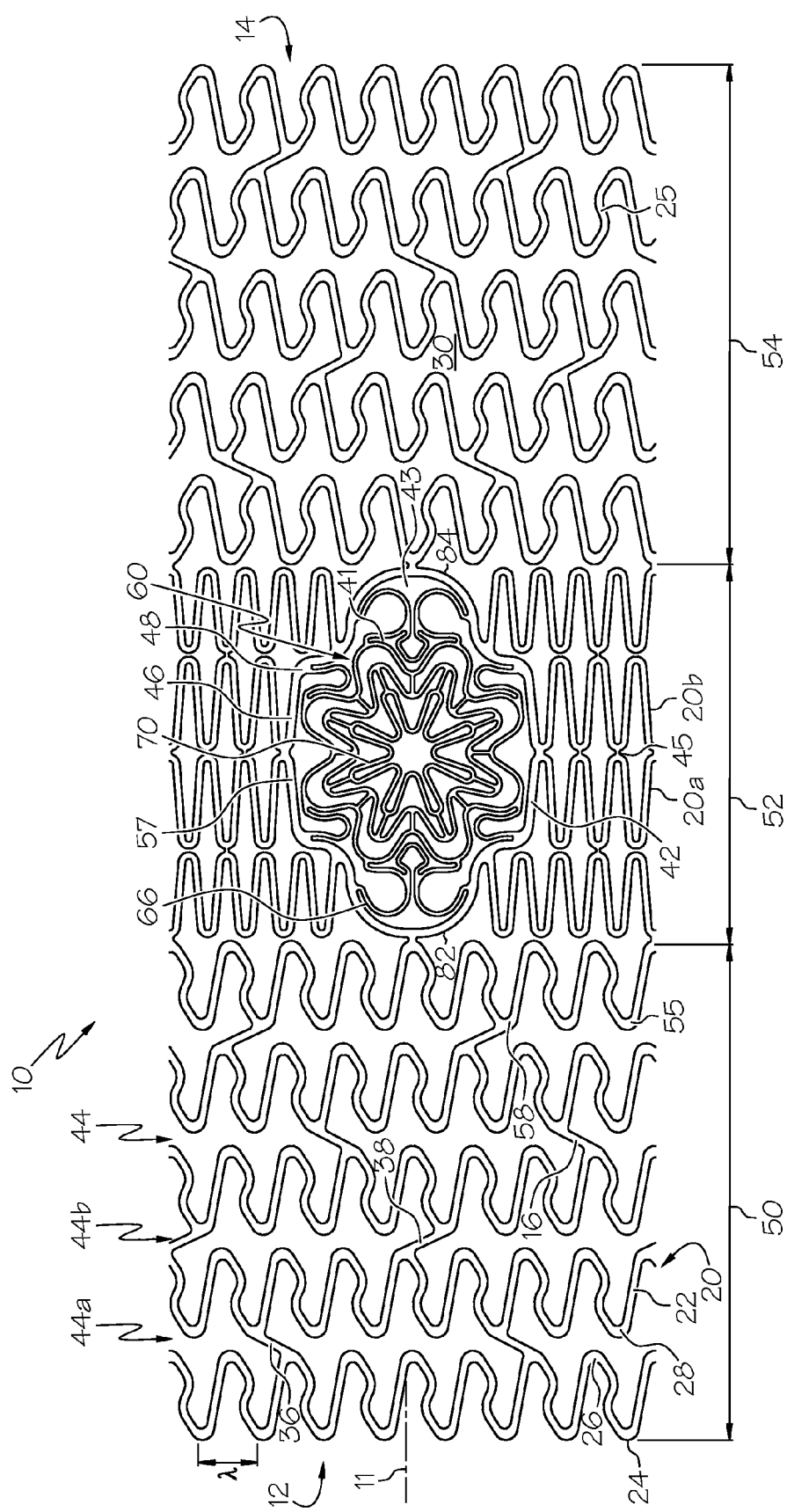

FIG. 8 shows a flat pattern for another embodiment of a stent 10 comprising another embodiment of a support ring 42 and further embodiments of side branch outer connectors 66.

In some embodiments, each distal valley 26 of one serpentine band 20a can be connected to a proximal peak 24 of an adjacent serpentine band 20b. In some embodiments, a connector column 44 can comprise direct connections or short connecting segments 45 between turns 28 of adjacent serpentine bands 20a, 20b.

Figure 9:
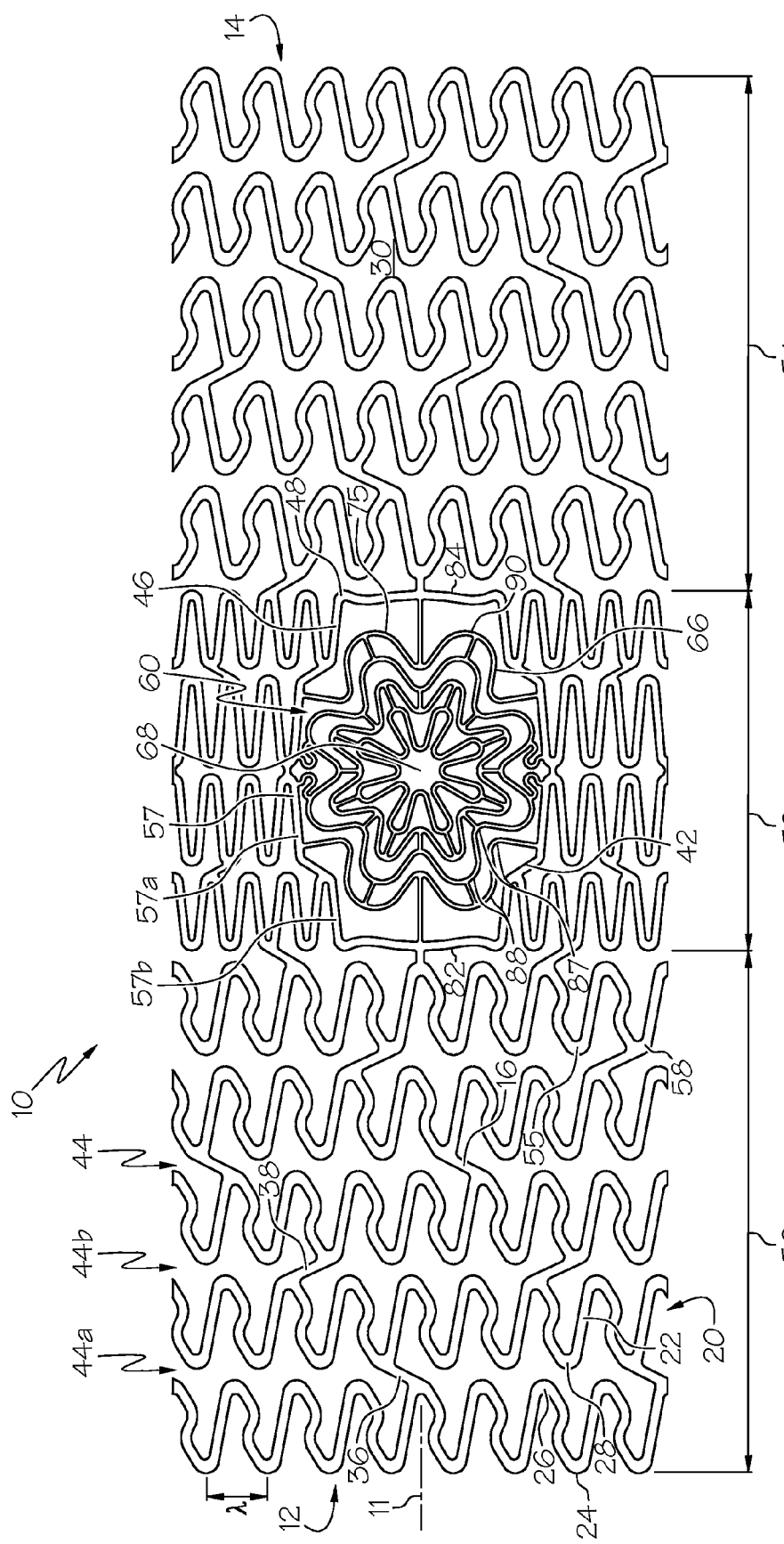

FIG. 9 shows a flat pattern for another embodiment of a stent 10 comprising another embodiment of a support ring 42 and further embodiments of side branch outer connectors 66.

In some embodiments, a first portion 82 of the support ring 42 comprises a mirror image of a second portion 84 taken across a circumference of the stent that intersects the side branch center point 68.

In some embodiments, each portion 82, 84 of the support ring 42 comprises a plurality of continuation struts 57 that each comprise a continuation of a serpentine band 20.

In some embodiments, a continuation strut 57 comprises the same width as a strut 22 of the serpentine band 420 to which it connects.

In some embodiments, a portion 82, 84 of the support ring 42 comprises a first continuation strut 57a that connects to one serpentine band 20, and a second continuation strut 57b that connects to another serpentine band 20.

In some embodiments, at least a portion of a side branch outer connector 66 is shaped to form a portion of partial fourth serpentine ring 75. Thus, a side branch outer connector can comprise multiple curved portions 90 with alternating concavity.

In some embodiments, a curved portion 90 of a side branch outer connector 66 can comprise an outer turn 88 of the partial fourth serpentine ring 75, wherein the curved portion 90 is concave with respect to the side branch center point 68. The curved portion 90 can further be aligned with an outer turn 88 of the third serpentine ring 74 in a side branch radial direction. Thus, a line oriented in a side branch radial direction that bisects an outer turn 88 of the third serpentine ring 74 can also bisect a curved portion 90 of a side branch outer connector 66.

In some embodiments, a curved portion 90 of a side branch outer connector 66 can comprise an inner turn 87 of the partial fourth serpentine ring 75, wherein the curved portion 90 is convex with respect to the side branch center point 68. The curved portion 90 can further be aligned with an inner turn 87 of the third serpentine ring 74 in a side branch radial direction. Thus, a line oriented in a side branch radial direction that bisects an inner turn 87 of the third serpentine ring 74 can also bisect a curved portion 90 of a side branch outer connector 66.

Figure 10:
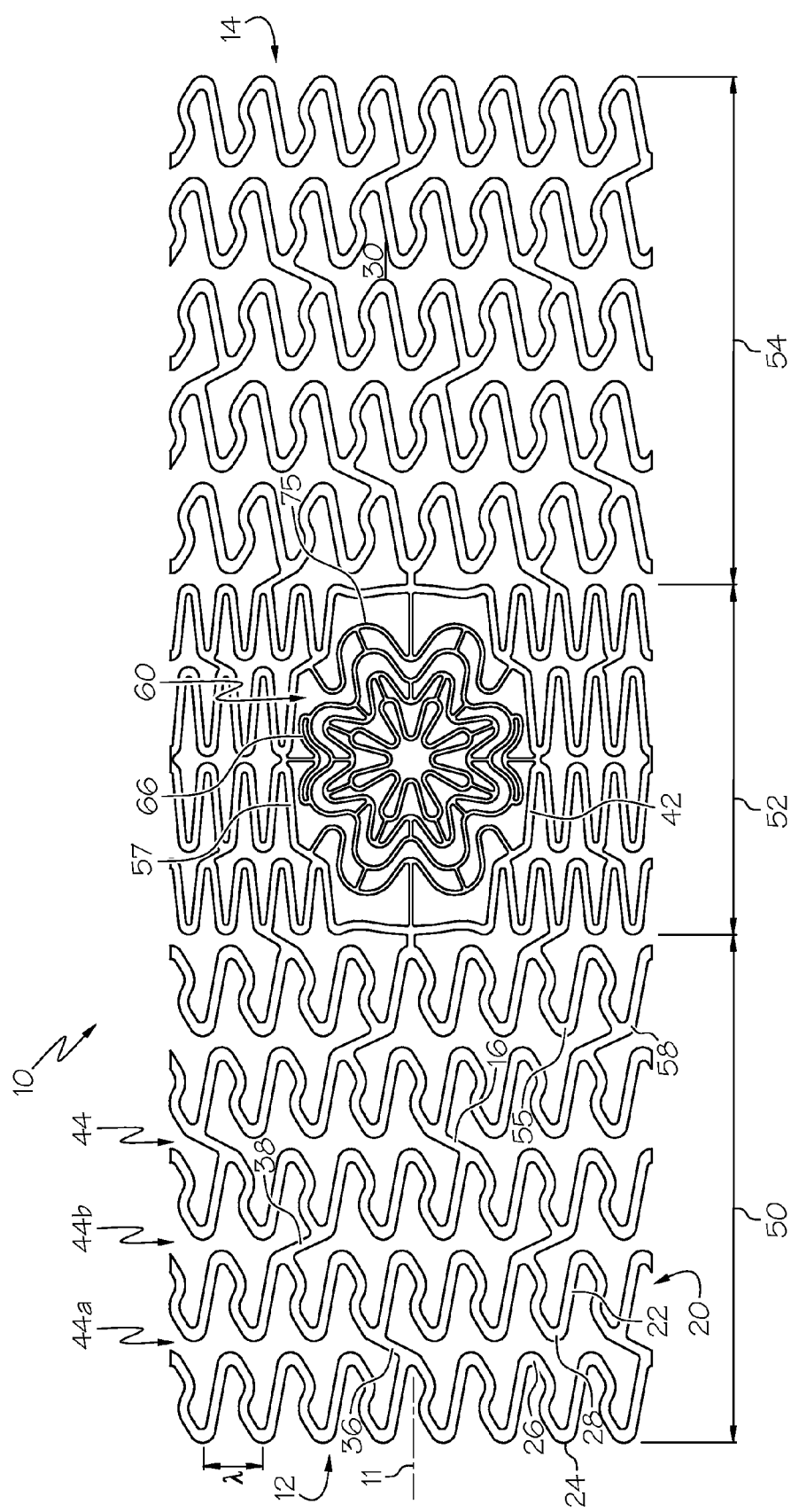

FIG. 10 shows a flat pattern for another embodiment of a stent 10 that is similar to FIG. 9 but comprises alternative embodiments of side branch outer connectors 66.

Figure 11:
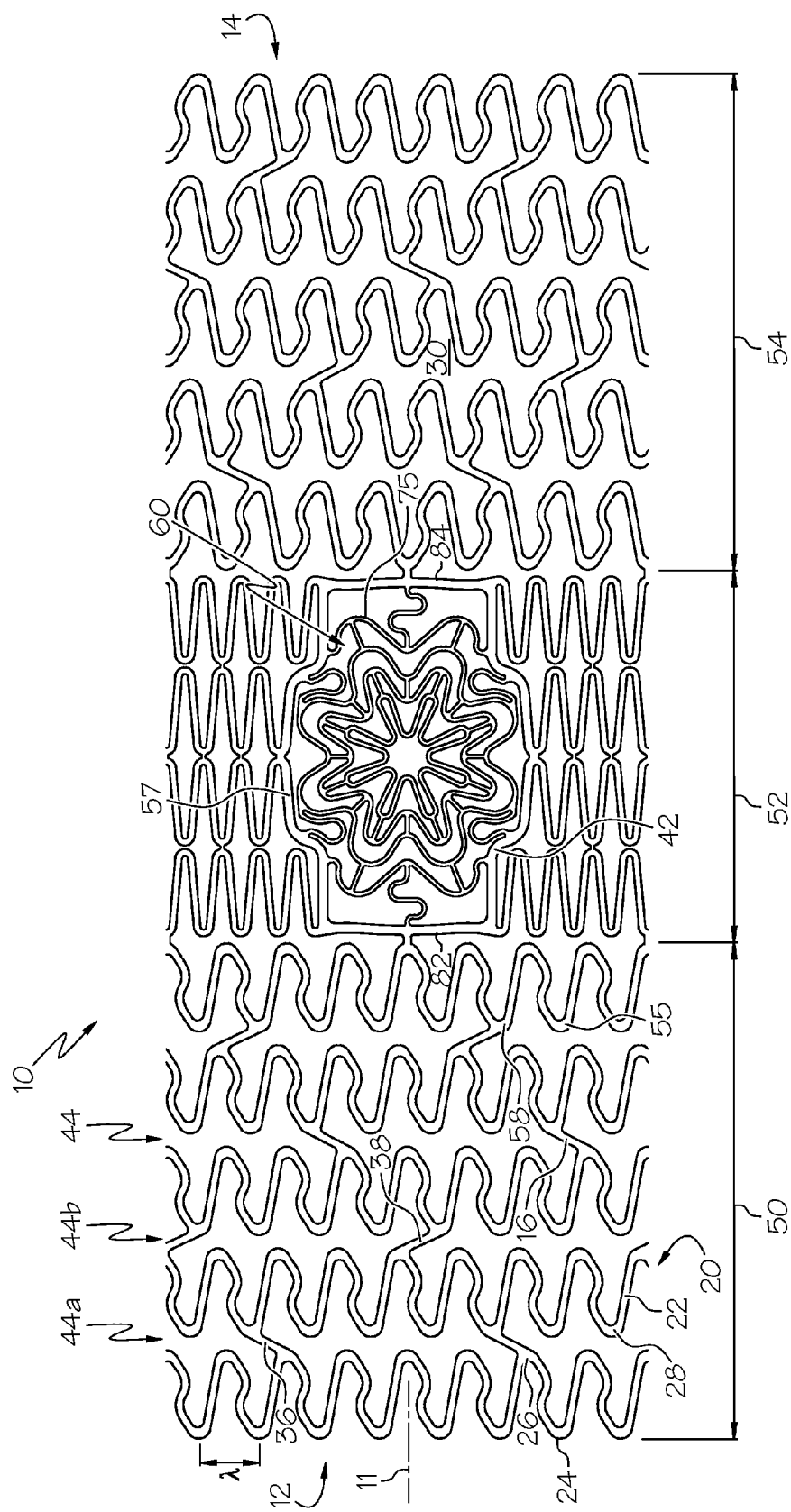

FIG. 11 shows a flat pattern for another embodiment of a stent 10 that is similar to FIG. 9 but comprises an alternative embodiment of a support ring 42 and alternative embodiments of side branch outer connectors 66.

Figure 12:
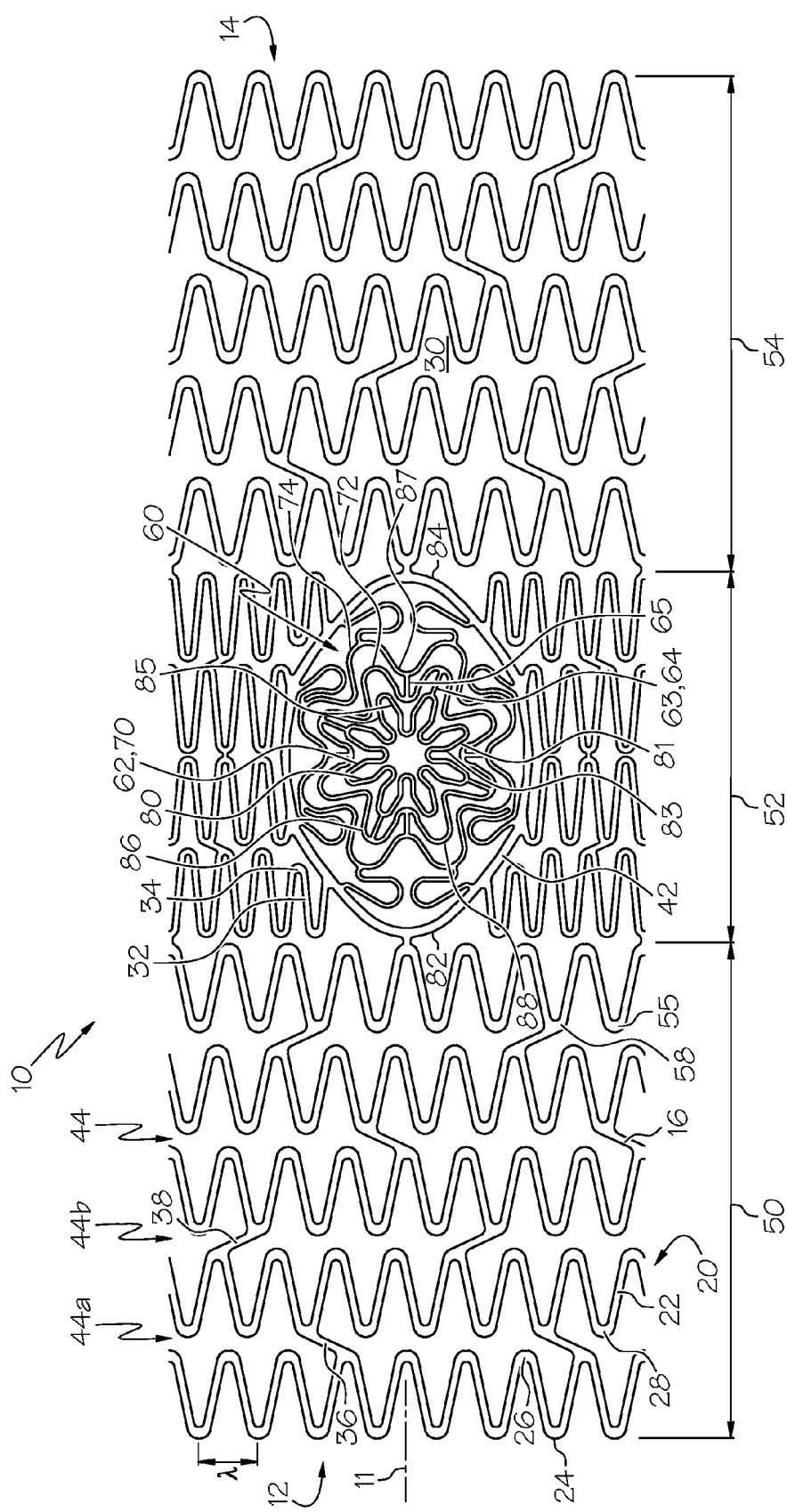

FIG. 12 shows a flat pattern for another embodiment of a stent 10.

In some embodiments, the first serpentine ring 70 comprises struts 80 that include a bend 83. In some embodiments, a strut 80 of a serpentine ring 62, 70 comprises multiple straight portions 81 and a bend 83.

In some embodiments, a serpentine ring 62 comprises a plurality of strut pairs 85. Each strut pair 85 comprises two struts 80, wherein the struts 80 of the pair 85 are mirror images of one another taken across a side branch radial line, such as a side branch radial line that bisects a turn 86 of a serpentine ring 62.

In some embodiments, a serpentine ring 62 comprises turns 86 that are not connected to a side branch connector 65. For example, in some embodiments, the first serpentine ring 70 and the second serpentine ring 72 comprise outer turns 88 that are not connected to a side branch inner connector 64. In some embodiments, every other outer turn 88 of the first serpentine ring 70 and the second serpentine ring 72 are connected to a side branch inner connector 64. In some embodiments, the second serpentine ring 72 and the third serpentine ring 74 comprise inner turns 87 that are not connected to a side branch intermediate connector 65. In some embodiments, every other inner turn 87 of the second serpentine ring 72 and the third serpentine ring 74 are connected to a side branch intermediate connector 65.

Figure 13:
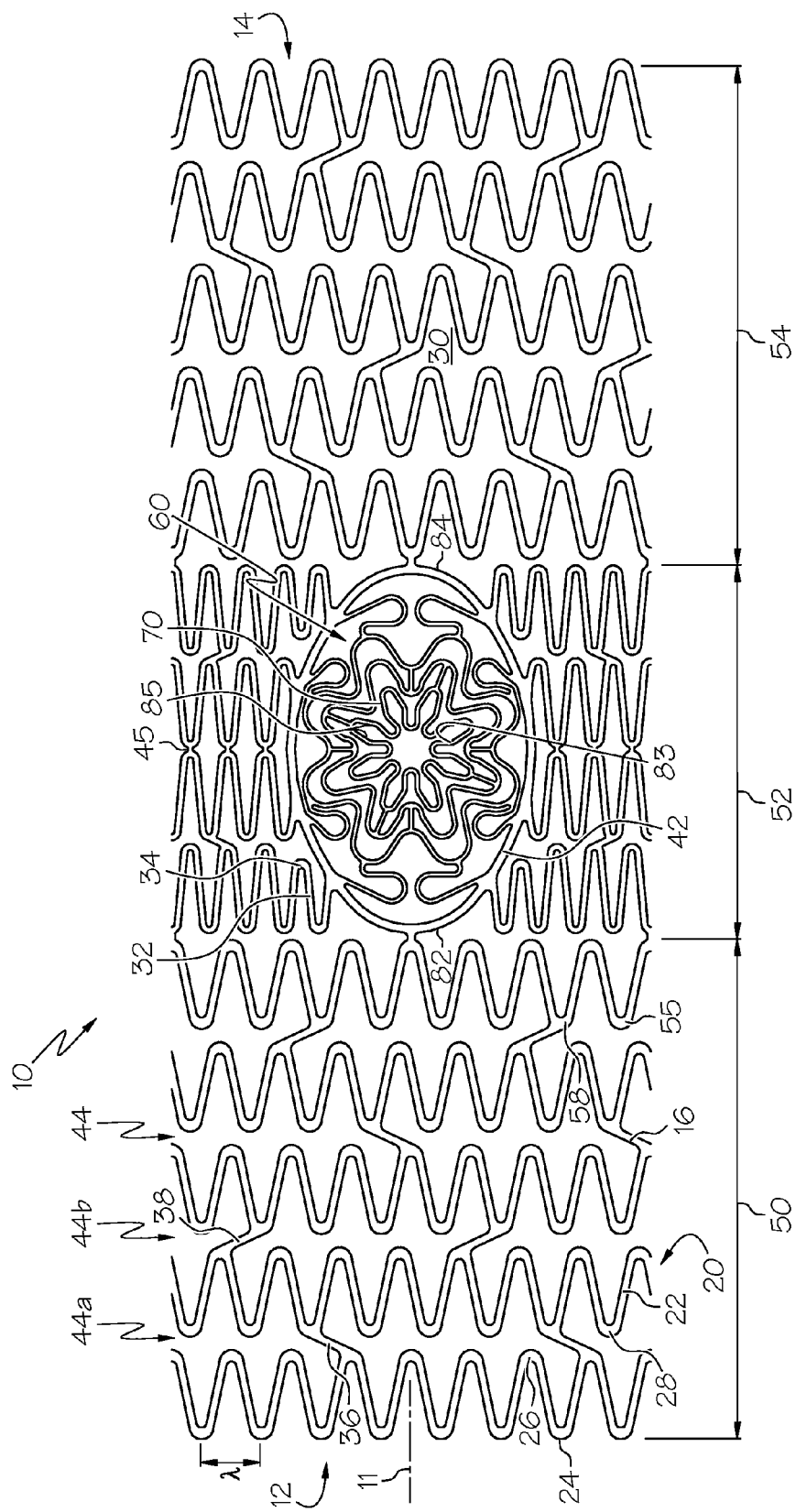

FIG. 13 shows a flat pattern for another embodiment of a stent 10 that is similar to FIG. 12, wherein each distal valley 26 of one serpentine band 20a is connected to a proximal peak 24 of an adjacent serpentine band 20b by a direct connection or short connecting segment 45.

Figure 14:
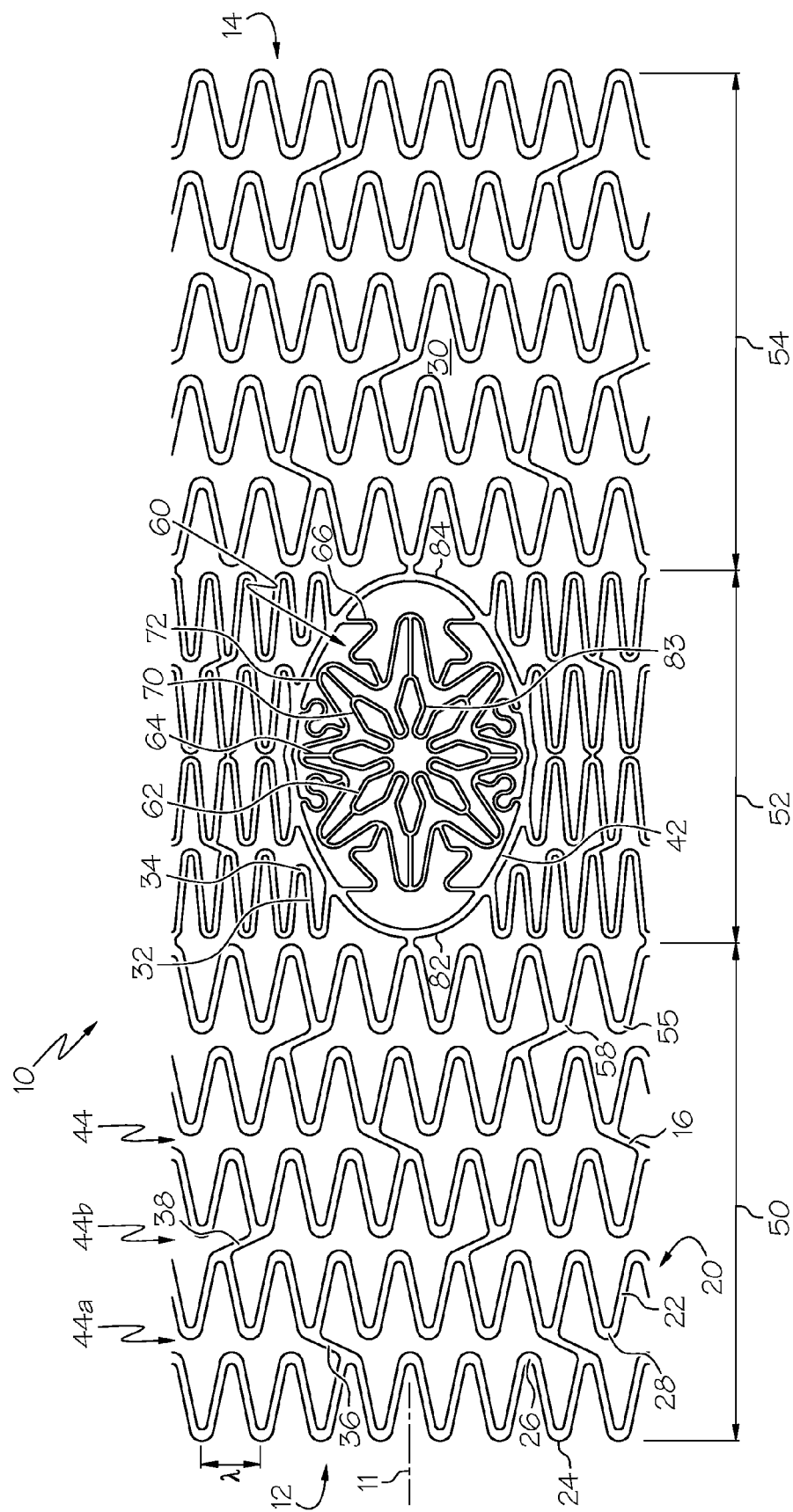

FIG. 14 shows a flat pattern for another embodiment of a stent 10 wherein the side branch rings 62 comprise a first serpentine ring 70 and a second serpentine ring 72. In some embodiments, the second serpentine ring 72 comprises an outer serpentine ring. In some embodiments, the side branch outer connectors 66 connect between the second serpentine ring 72 and the support ring 42.

Figure 16:
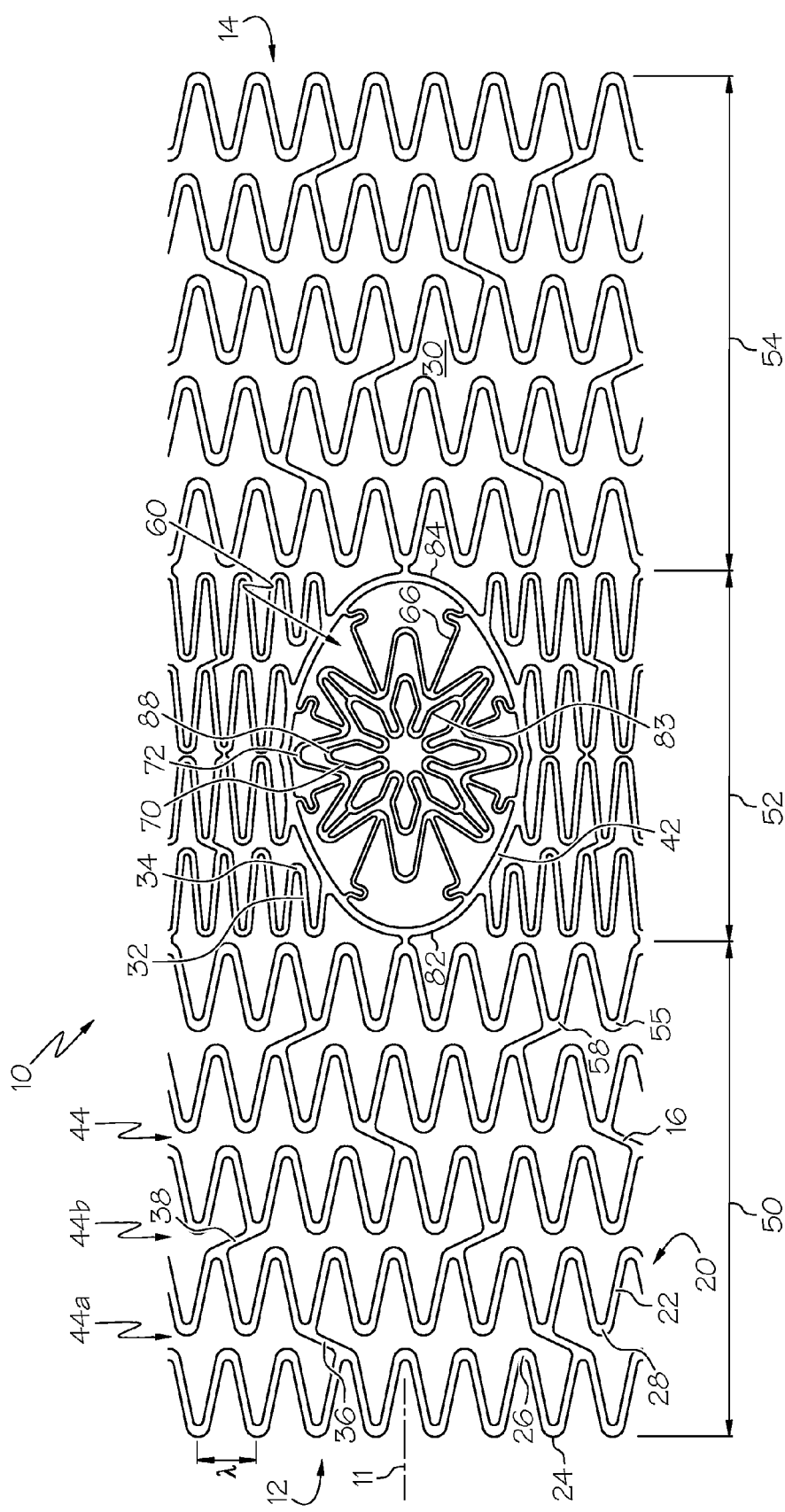

FIGS. 15 and 16 each show a flat pattern for another embodiment of a stent 10 that is similar to FIG. 14, wherein the first serpentine ring 70 and the second serpentine ring 72 comprise outer turns 88 that are not connected to a side branch inner connector 64. FIGS. 15 and 16 also show alternative embodiments of side branch outer connectors 66.

FIG. 15A shows a three-dimensional view of an embodiment of a stent 10 having a side branch structure 60 similar to the side branch structure 60 shown the pattern of FIG. 15. The stent 10 is shown in a nominal or unexpanded configuration with the side branch structure 60 forming a portion of the generally cylindrical stent body structure.

FIG. 15B shows the stent of FIG. 15A in an expanded configuration with the side branch structure 60 outwardly deployed. The serpentine bands 20 form a generally cylindrical stent body structure that extends around the stent longitudinal axis 11. The side branch structure 60 extends in a radial outward direction above the generally cylindrical stent body structure. Portions of the outwardly deployed side branch structure 60 are located farther away from the stent longitudinal axis 11 than portions of the stent 10 that form the generally cylindrical stent body structure.

The outwardly deployed side branch rings 62 form a tubular structure having a side branch axis 15 that is nonparallel to the stent longitudinal axis 11. In some embodiments, the side branch axis 15 is orthogonal to the stent longitudinal axis 11.

FIG. 15C shows an end view of the stent 10 shown in FIG. 15B.

Figure 17:
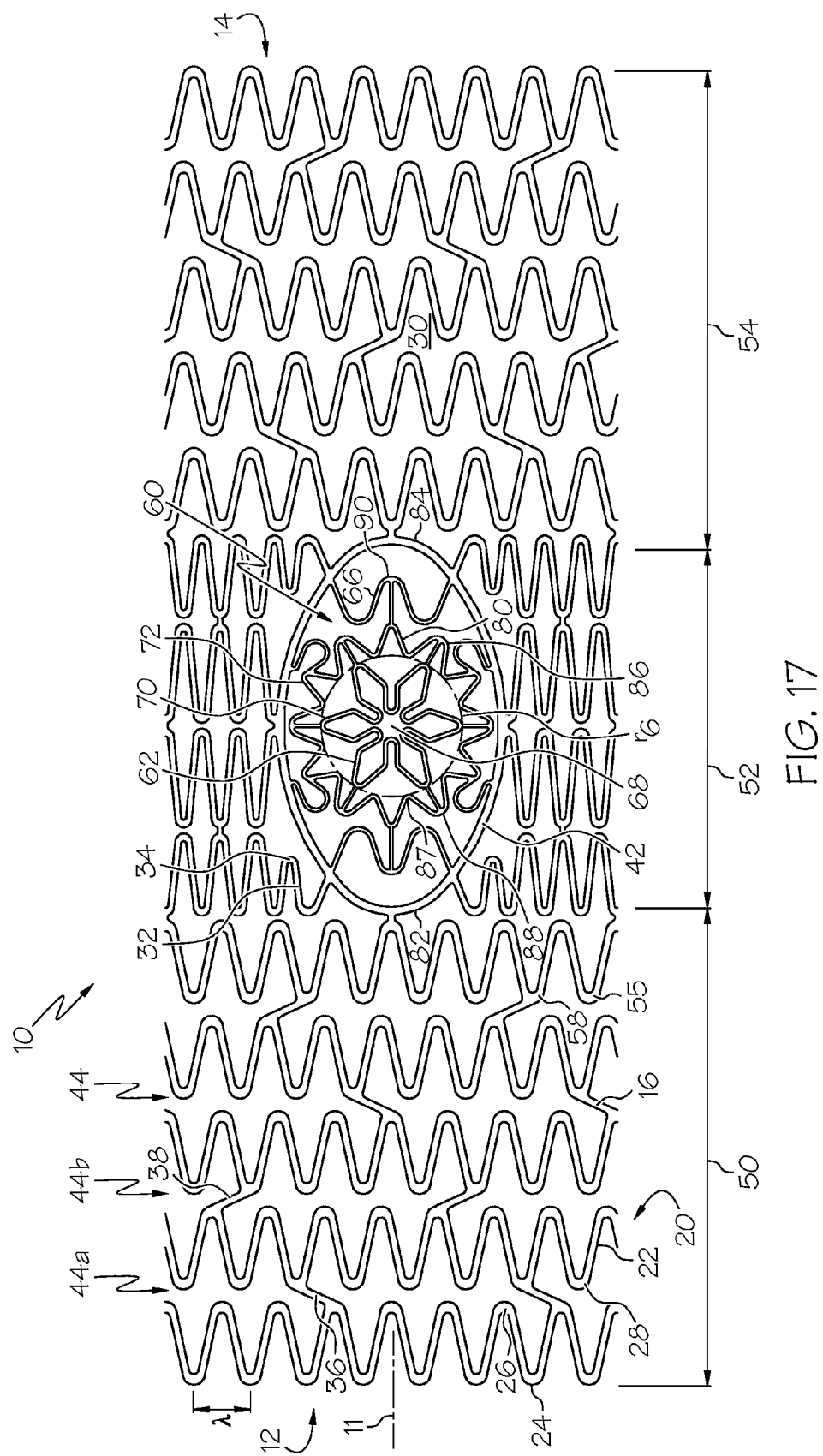

FIG. 17 shows a flat pattern for another embodiment of a stent 10.

In some embodiments, the side branch rings 62 can comprise different numbers of struts 80 and turns 86. In some embodiments, the second serpentine ring 72 can have more struts 80 and more turns 86 than the first serpentine ring 70. In some embodiments, the second serpentine ring 72 can have more inner turns 87 and more outer turns 88 than the first serpentine ring 70.

In some embodiments, each outer turn 88 of the first serpentine ring 70 is aligned with an outer turn 88 of the second serpentine ring 72 in a side branch radial direction. Further, each inner turn 87 of the first serpentine ring 70 is aligned with an outer turn 88 of the second serpentine ring 72 in a side branch radial direction. Thus, the second serpentine ring 72 can comprise inner turns 87 that are not aligned with turns 86 of the first serpentine ring 70 in a side branch radial direction.

In some embodiments, the outer turns 88 of the first serpentine ring 70 and the inner turns 87 of the second serpentine ring 72 are aligned around a common reference circle $r_6$ that is centered on the side branch center point 68.

FIG. 17 also shows further embodiments of side branch outer connectors 66.

Figure 18:
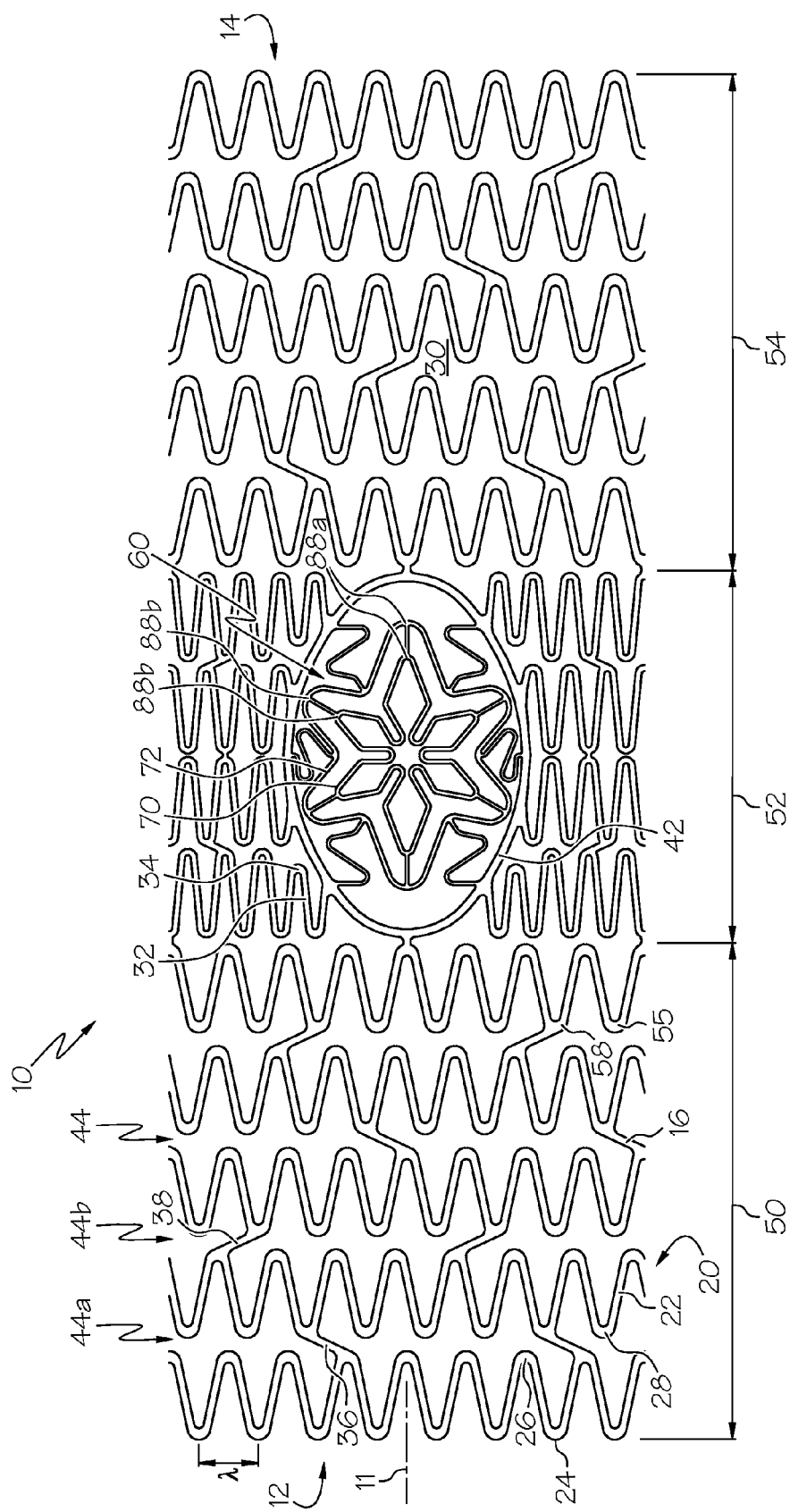
Figure 19:
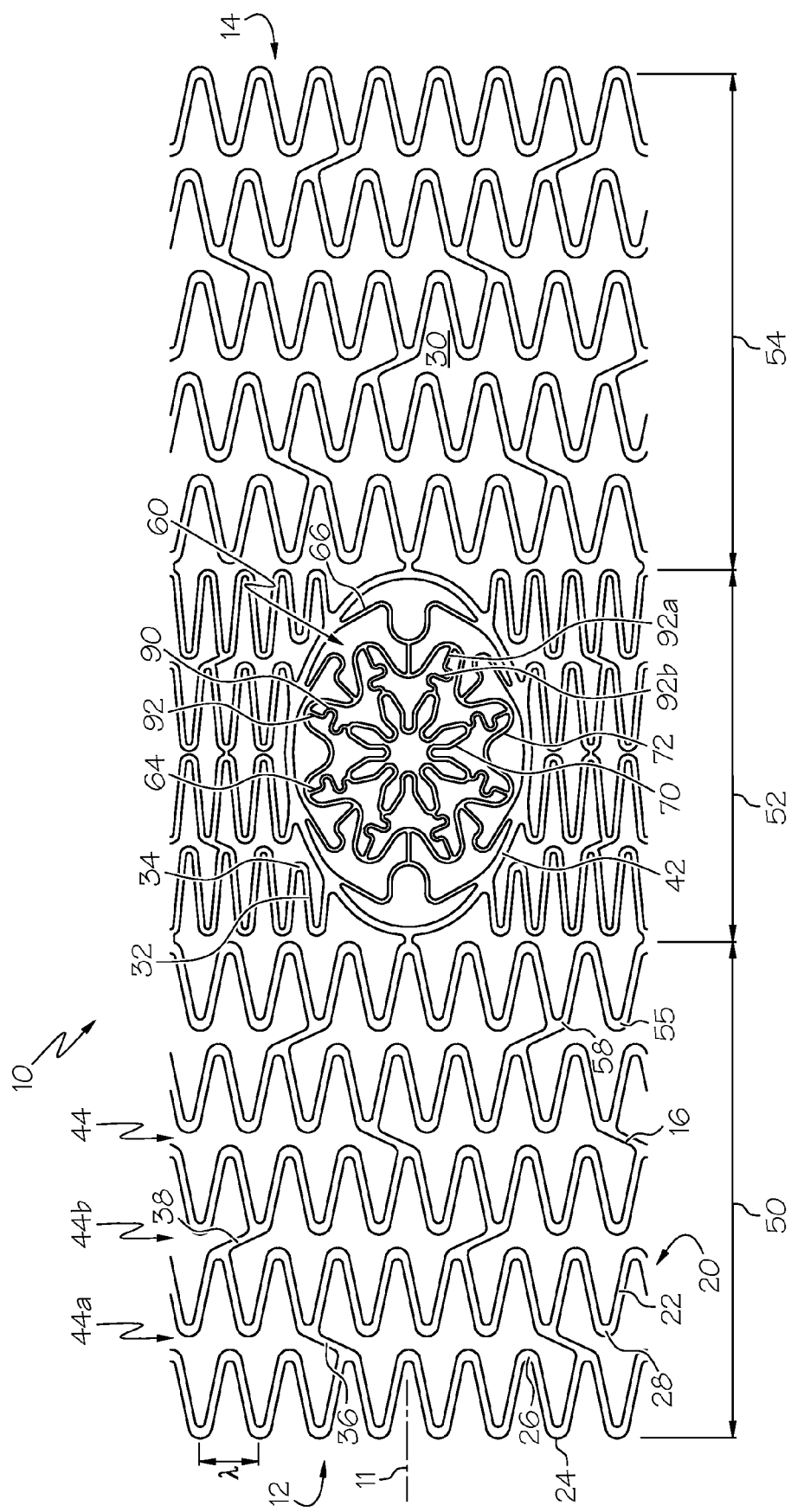

FIG. 18 shows a flat pattern for another embodiment of a stent 10.

In some embodiments, the first serpentine ring 70 comprises outer turns 88a that are located farther away from the side branch center point 68 than other outer turns 88b of the first serpentine ring 70. In some embodiments, the second serpentine ring 72 comprises outer turns 88a that are located farther away from the side branch center point 68 than other outer turns 88b of the second serpentine ring 72.

FIG. 18 shows a flat pattern for another embodiment of a stent 10.

In some embodiments, a side branch inner connector 64 comprises at least one portion that is not oriented in a side branch radial direction. In some embodiments, a side branch inner connector 64 comprises at least one straight portion 92 and at least one curved portion 90. In some embodiments, a side branch inner connector 64 comprises a multiple curved portions 90 having different or opposite concavities. In some embodiments, a side branch inner connector 64 comprises multiple straight portions 92 that are nonparallel to one another. For example, in some embodiments, a first straight portion 92a is oriented in a side branch radial direction, and a second straight portion 92b is oriented orthogonal to the first straight portion 92a

The inventive stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Pachtaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent comprising:
a plurality of interconnected framework members defining a plurality of cells, a portion of the interconnected framework members comprising a side branch structure defining an inner side branch cell, the inner side branch cell being shaped differently than other cells of the stent;
the side branch structure comprising:
a first serpentine ring extending around and defining the inner side branch cell, the first serpentine ring comprising alternating inner turns and outer turns, the outer turns aligned upon a first reference circle;
a second serpentine ring circumferentially surrounding the first serpentine ring, the second serpentine ring comprising alternating inner turns and outer turns, the inner turns aligned upon a second reference circle; and
a plurality of inner side branch connectors, each inner side branch connector spanning between the first serpentine ring and the second serpentine ring in a side branch radial direction;
wherein the first reference circle has a greater diameter than the second reference circle.

2. The stent of claim 1, wherein each side branch connector spans between an outer turn of the first serpentine ring and an outer turn of the second serpentine ring.

3. The stent of claim 1, wherein each outer turn of the first serpentine ring is aligned with an outer turn of the second serpentine ring in a side branch radial direction.

4. The stent of claim 1, wherein the first reference circle is concentric with the second reference circle.

5. The stent of claim 1, wherein the outer turns of the second serpentine ring are aligned upon a third reference circle;
the side branch structure further comprising a third serpentine ring surrounding the second serpentine ring, the third serpentine ring comprising alternating inner turns and outer turns, the inner turns aligned upon a fourth reference circle;
wherein the third reference circle has a greater diameter than the fourth reference circle.

6. The stent of claim 5, the further comprising a plurality of intermediate side branch connectors, each intermediate side branch connector spanning between the second serpentine ring and the third serpentine ring in a side branch radial direction.

7. The stent of claim 6, wherein each intermediate side branch connector spans between an inner turn of the second serpentine ring and an inner turn of the third serpentine ring.

8. The stent of claim 5, further comprising a support ring that extends continuously around the third serpentine ring, the support ring comprising a strut width that is greater than a strut width of any portion of the side branch structure.

9. The stent of claim 8, wherein the support ring is continuously concave with respect to the inner side branch cell.

10. The stent of claim 8, further comprising a plurality of side branch outer connectors that connect between the third serpentine ring and the support ring.

11. A stent comprising:
a plurality of interconnected framework members defining a plurality of cells, a portion of the interconnected framework members comprising a side branch structure defining an inner side branch cell, the inner side branch cell being shaped differently than other cells of the stent;
the side branch structure comprising:
a first serpentine ring extending around and defining the inner side branch cell, the first serpentine ring comprising alternating inner turns and outer turns;
a second serpentine ring circumferentially surrounding the first serpentine ring, the second serpentine ring comprising alternating inner turns and outer turns, the second serpentine ring having the same number of outer turns as the first serpentine ring; and
a plurality of side branch connectors, each side branch connector spanning between the first serpentine ring and the second serpentine ring in a side branch radial direction.

12. The stent of claim 11, wherein each outer turn of the first serpentine ring is aligned with an outer turn of the second serpentine ring in a side branch radial direction.

13. The stent of claim 11, wherein the aligned outer turns are centered upon a side branch radial axis.

14. The stent of claim 11, wherein the outer turns of the first serpentine ring are aligned upon a first reference circle; and the inner turns of the second serpentine ring are aligned upon a second reference circle, the first reference circle having a greater diameter than the second reference circle.

15. The stent of claim 11, wherein each side branch connector spans between an outer turn of the first serpentine ring and an outer turn of the second serpentine ring.

16. The stent of claim 11, the first serpentine ring comprising struts extending between said inner turns and outer turns, wherein each strut of the first serpentine ring comprises a bend.

17. The stent of claim 16, wherein the struts of the first serpentine ring comprise a plurality of pairs, the struts of a pair comprising mirror images of one another taken across a side branch radial axis.

18. A stent comprising:
a plurality of interconnected framework members defining a plurality of cells, a portion of the interconnected framework members comprising a side branch structure defining an inner side branch cell, the inner side branch cell being shaped differently than other cells of the stent;
the side branch structure comprising:
a first serpentine ring extending around and defining the inner side branch cell, the first serpentine ring comprising alternating inner turns and outer turns, the outer turns aligned upon a first reference circle;
a second serpentine ring circumferentially surrounding the first serpentine ring, the second serpentine ring comprising alternating inner turns and outer turns, the inner turns aligned upon a second reference circle, the outer turns aligned upon a third reference circle; and
a third serpentine ring surrounding the second serpentine ring, the third serpentine ring comprising alternating inner turns and outer turns, the inner turns aligned upon a fourth reference circle;
wherein the first reference circle has a greater diameter than the second reference circle, and the third reference circle has a greater diameter than the fourth reference circle.

19. The stent of claim 18, wherein the first, second, third and fourth reference circles are concentric.

20. The stent of claim 18, the side branch structure further comprising a plurality of side branch connectors connected between the first serpentine ring and the second serpentine ring, each side branch connector oriented in a side branch radial direction.

* * * * *